(12) United States Patent
Mouzannar

(10) Patent No.: US 11,760,976 B2
(45) Date of Patent: Sep. 19, 2023

(54) STEM CELLS AND DECELLULARIZATION OF TISSUE MATRIX FROM CORD TISSUE

(71) Applicant: STEM CELL RESERVE LP, Houston, TX (US)

(72) Inventor: Raymond Mouzannar, Houston, TX (US)

(73) Assignee: STEM CELL RESERVE, LP, Houston, TX (US)

( * ) Notice: Subject to any disclaimer, the term of this patent is extended or adjusted under 35 U.S.C. 154(b) by 283 days.

(21) Appl. No.: 17/081,701

(22) Filed: Oct. 27, 2020

(65) Prior Publication Data

US 2021/0071144 A1 Mar. 11, 2021

Related U.S. Application Data

(60) Division of application No. 15/613,264, filed on Jun. 5, 2017, now Pat. No. 10,851,345, which is a continuation-in-part of application No. 13/890,134, filed on May 8, 2013, now Pat. No. 9,670,457.

(60) Provisional application No. 61/644,423, filed on May 8, 2012.

(51) Int. Cl.
```
C12N 5/0775      (2010.01)
A61L 27/38       (2006.01)
C12N 5/073       (2010.01)
```

(52) U.S. Cl.
CPC ........ *C12N 5/0665* (2013.01); *A61L 27/3834* (2013.01); *A61L 27/3895* (2013.01); *C12N 5/0605* (2013.01); *C12N 2500/02* (2013.01); *C12N 2502/137* (2013.01); *C12N 2509/10* (2013.01); *C12N 2513/00* (2013.01); *C12N 2533/90* (2013.01)

(58) Field of Classification Search
None
See application file for complete search history.

(56) References Cited

U.S. PATENT DOCUMENTS

2010/0330047 A1* 12/2010 Valorani ................. A61P 17/02
435/375

OTHER PUBLICATIONS

Le Blanc, Katarina; et al; "Generation of Immunosuppressive Mesenchymal Stem Cells in Allogeneic Human Serum" Transplantation, 84, 1055-1059, 2007 (Year: 2007).*

Wagner, John E; et al; "Transplantation of unrelated donor umbilical cord blood in 102 patients with malignant and nonmalignant diseases: influence of CD34cell dose and HLA disparity on treatment-related mortality and survival" Blood, 100, 1611-1618, 2002 (Year: 2002).*

* cited by examiner

*Primary Examiner* — David W Berke-Schlessel
(74) *Attorney, Agent, or Firm* — Boulware & Valoir, PLLC

(57) ABSTRACT

Methods and products obtained from the method for isolating and culturing mixed populations of stem cells, making decellularized tissue matrix, making decellularized tissue matrix infused with said mixed populations of stem cells, and methods of stem cell therapy are provided.

12 Claims, 9 Drawing Sheets

Figure 2: Schematic diagram showing the different possible uses of cord blood cells, cord tissue cells, cord matrices alone or in combination to treat a degenerated tissue.

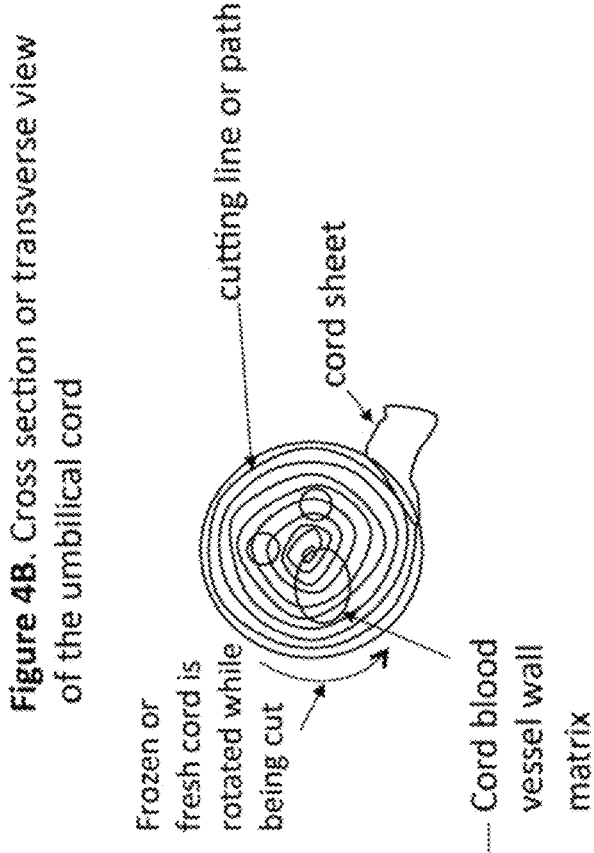
Figure 4A. Lateral view of an umbilical cord
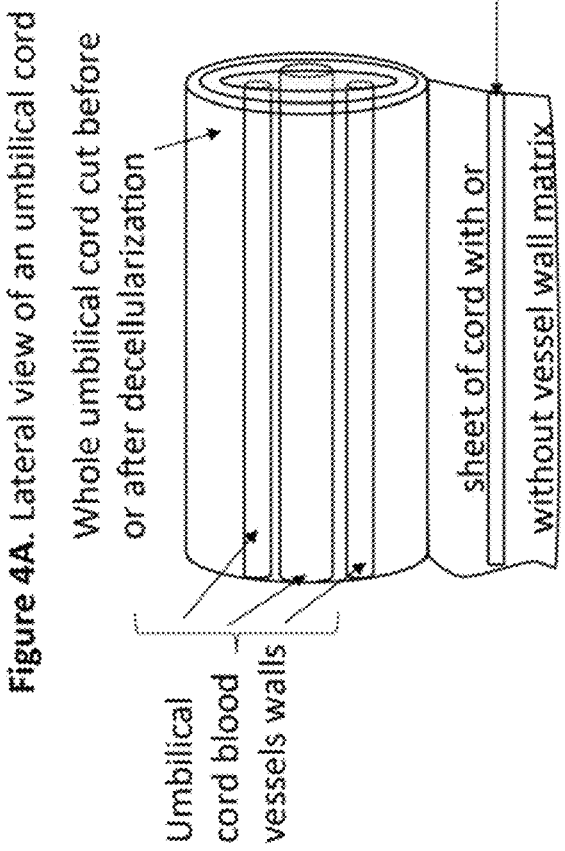
Figure 4B. Cross section or transverse view of the umbilical cord

STEM CELLS AND DECELLULARIZATION OF TISSUE MATRIX FROM CORD TISSUE

CROSS-REFERENCE TO RELATED APPLICATIONS

This invention is a divisional application of, and claims priority to, U.S. continuation-in-part application Ser. No. 15/613,264, filed Jun. 5, 2017 which claims priority of non-provisional U.S. application Ser. No. 13/890,134, filed May 8, 2013, which claims priority to U.S. Provisional Application No. 61/644,423, filed May 8, 2012, each of which is expressly incorporated by reference in its entirety for all purposes herein.

FEDERALLY SPONSORED RESEARCH STATEMENT

Not applicable.

BACKGROUND OF THE INVENTION

Stem cells are unspecialized cells that have two defining properties: the ability to differentiate into other cells and the ability to self-regenerate. The ability to differentiate is the potential to develop into other cell types. A totipotent stem cell (e.g. fertilized egg) can develop into all cell types including the embryonic membranes. A pluripotent stem cell can develop into cells from all three germinal layers (e.g., cells from the inner cell mass). Other cells can be oligopotent, bipotent or unipotent depending on their ability to develop into few, two or one other cell type(s). Self-regeneration is the ability of stem cells to divide and produce more stem cells. During early development, stem cell division is believed to be symmetrical i.e. each cell divides to give rise to daughter cells, each with the same potential. Later in development, stem cells are believed to divide asymmetrically with one of the daughter cells produced being a stem cell and the other a more differentiated cell (Sharpless N. E. and De Pinho R. A., "How stem cells age and why this makes us grow old", Nature Rev. MCB, 2007)

Stem cells are further classified according to their differentiation potential, roughly as follows:

| Differentiation Potential | Number of cell types | Example of stem cell | Cell types resulting from differentiation |
|---|---|---|---|
| Totipotential | All | Zygote (fertilized egg), blastomere | All cell types |
| Pluripotential | All except cells of the embryonic membranes | Cultured human ES cells | Cells from all three germ layers |
| Multipotential | Many | Hematopoietic cells | skeletal muscle, cardiac muscle, liver cells, all blood cells |
| Oligopotential | Few | Myeloid precursor | 5 types of blood cells (Monocytes, macrophages, eosinophils, neutrophils, erythrocytes) |
| Quadripotential | 4 | Mesenchymal progenitor cell | Cartilage cells, fat cells, stromal cells, bone-forming cells |
| Tripotential | 3 | Glial-restricted precursor | 2 types of astrocytes, oligodendrocytes |
| Bipotential | 2 | Bipotential precursor from murine fetal liver | B cells, macrophages |
| Unipotential | 1 | Mast cell precursor | Mast cells |
| Nullipotential | None | Terminally differentiated cell e.g. Red blood cell | No cell division |

As development proceeds, there is a loss of potential and a gain of specialization, a process called determination. For example, the cells of the germ layers are more specialized than the fertilized egg or the blastomere. The germ layer stem cells give rise to progenitor cells (also known as progenitors or precursor cells). For example, a cell in the endoderm gives rise to a primitive gut cell (progenitor), which can further divide to produce a liver cell (a terminally differentiated cell).

While there is consensus in the literature that a progenitor is a partially specialized type of stem cell, there are differences in how progenitor cell division is described. For instance, according to one source, when a stem cell divides at least one of the daughter cells it produces is also a stem cell; when a progenitor cell undergoes cell division it produces two specialized cells. A different source, however, explains that a progenitor cell undergoes asymmetrical cell division, while a stem cell undergoes symmetrical cell division.

The different kinds of human stem cells identified to date include: embryonic stem cells derived from embryos artificially produced in in-vitro fertility clinics, fetal stem cells derived from aborted fetuses, umbilical cord blood and placental blood stem cells, umbilical cord and placental tissue stem cells, bone marrow blood stem cells, peripheral blood stem cells, bone marrow mesenchymal stem cells, adult fat or adipose tissue-derived stem cells, cardiac muscle stem cells, skin epidermis stem cells, endothelial progenitor cells, brain and spinal cord derived neural stem cells, dental pulp stem cells and olfactory epithelium stem cells. In addition, human embryonic-like stem cells can be synthetically manufactured by inducing any adult terminally differentiated cell like a cheek skin fibroblast or even an adult stem cell into an embryonic-like stem cell.

Stem cells of the umbilical cord tissue are defined as mesenchymal stem cells or stromal stem cells with set characteristics. However, not all umbilical cord tissue cells have been tested for stem cell activity. Cord tissue mesenchymal stem cells have an ability to adhere to laboratory flask or dish surfaces and their morphology is fibroblast-like. They are believed to express specific surface markers like CD105, CD133, CD166, CD44, CD54, CD90, HLA-ABC, CD146, CD73, STRO-1 and are capable of differentiating into chondrocytes, cardiomyocytes, adipocytes and osteocytes. Cord tissue mesenchymal stem cells are expected to engraft better than bone marrow mesenchymal stem cells or blood stem cells because unlike older tissue or bone marrow derived mesenchymal stem cells, they do not express a mature set of major histocompatibility antigens.

However, there are also inconsistencies in how stem cells are described and/or identified, making the field a challenging one to understand, and the literature is replete with inconsistencies. Mendicino M. et. al., (2014) "MSC-Based Product Characterization for Clinical Trials: An FDA Perspective", Cell Stein Cell 14, Feb 6.

The ability of stem cells to self-renew and give rise to subsequent generations with variable degrees of differentiation capacity offers significant potential to replace diseased and damaged areas in the body, with minimal risk of rejection and side effects. Many medical researchers believe that stem cell treatments have the potential to change the face of human disease and human tissue degeneration. Although unidentified back then, stem cells were used in tribal medicine thousands of years ago when tribe medical leaders looked for "young" blood to treat sick tribe members that would be regarded today as consanguineous people.

A number of stem cell therapies already exist, but most are at experimental stages, with the notable exception of bone marrow and cord blood transplantations. Whether experimental or not, stem cell therapies are also costly. Medical researchers anticipate that adult and embryonic stem cells will soon be able to treat cancer, Type 1 diabetes mellitus, Parkinson's disease, Huntington's disease, Celiac Disease, cardiac failure, muscle damage and neurological disorders, and many others. Nevertheless, more research is necessary to further understand stem cell behavior before and after processing and upon transplantation as well as the mechanisms of stem cell interaction with the diseased/injured microenvironment. Keating, A. (2012) "Mesenchymal Stromal Cells: New Directions", Cell Stem Cell 10, 709-716; Akkermann R., Beyer F., Küry P. (2017) "Heterogeneous populations of neural stem cells contribute to myelin repair", Neural Regen Res. Apr;12(4):509-517.

It is also important to note that it is not yet fully understood what factors define the environment of a cell or what factors define the normal biology of different cells during development, adulthood and aging. However, it is clear that ontogeny and age-related phenomena exert an effect on cells and environment thereof. Stem cells of different differentiation potentials are also defined by their source, age, preservation, culture and differentiation methods. Sisakhtnezhad S., Alimoradi E., Akrami H., (2017) External factors influencing mesenchymal stem cell fate in vitro, European Journal of Cell Biology, Vol 96, Issue 1, Pages 13-33.

According to clinicaltrials.gov, there has been a significant increase in human trials using different stem cells for various applications since 2009. These trials, however, rely on suboptimal cellular and matrix products either derived from mature adult people or prepared using suboptimal non-stem cell specific methods. For example, adult bone marrow or adipose tissue derived stem cell products cultured in two-dimensional environments under high oxygen pressure, not normally found in vivo. Mendicino M. et. al., (2014) "MSC-Based Product Characterization for Clinical Trials: An FDA Perspective", Cell Stem Cell 14, Feb 6.

The literature is also replete with products manufactured in ways that alter, reduce or increase rejection risk of the product, be it transplanted cells or matrices. For example, culturing human cord blood stem cells in the presence of adult human bone marrow mesenchymal stem cells can elicit an adverse immunoreactivity between the cultured cells or between the cultured cells and the host, hence reducing the desired regenerative effect of the assumed therapeutic product. In this case, adding fetal bovine or synthetic serum to the stem cell product in culture may further reduce the optimal biology of the stem cell product. DeLima M. et. al., 2012 Cord-Blood Engraftment with Ex Vivo Mesenchymal-Cell Coculture, NEJM 367;24; Gharibi B., Hughes F. J., (2012) Effects of Medium Supplements on Proliferation, Differentiation Potential, and In Vitro Expansion of Mesenchymal Stem Cells, Stem Cells Translational Medicine, 1:771-782. Emnett R. J. et. al., (2016) Evaluation of Tissue Homogenization to Support the Generation of GMP-Compliant Mesenchymal Stromal Cells from the Umbilical Cord. Stem Cells International. Article ID 3274054; Friedman R. et. al., (2007) Umbilical Cord Mesenchymal Stem Cells: Adjuvants for Human Cell Transplantation. Biology of Blood and Marrow Transplantation 13:1477-1486.

Spatial growing conditions also plays an important role in stem cell therapies. Using an ultra-thin supportive extracellular matrix as a synthetic product derived from cell cultures provides little three-dimensional environment to support cell growth and differentiation. Furthermore, a matrix derived from an animal or different human is often immunologically incompatible with cells used for regenerative medicine. There is an extreme shortage of organ donors and an extreme need of autologous or family related matrices and cells for regenerative medicine so as to avoid the complications associated with rejection and lifetime immunosuppression. Badylak Steven (2014) Decellularized Allogeneic and Xenogeneic Tissue as a Bioscaffold for Regenerative Medicine: Factors that Influence the Host Response. Annals of Biomedical Engineering, Vol. 42, No. 7.

Studies showed that "mesenchymal stem cells" grown in 2D dishes in the presence of allogeneic human umbilical cord serum show phenotypic differences at the structural level including smaller size, denser nuclear membrane, and a reduced cytoplasm as compared to cells grown in animal serum. Nevertheless, these same "mesenchymal stem cells" held their characteristic surface marker expression (HLA-DR, CD73, CD90, CD34, CD45, CD166, and CD105), despite their differences in structure, self-renewal, and proliferative capacities. Jung J. et. al., (2009) "Mesenchymal stromal cells expanded in human allogenic cord blood serum display higher self-renewal and enhanced osteogenic potential", Stem Cells and Development. 18(4):559-571; Phadnis S M et. al., (2006) "Human umbilical cord blood serum promotes growth, proliferation, as well as differentiation of human bone marrow-derived progenitor cells". In Vitro Cellular and Developmental Biology-Animal, 42(10):283-286. Smith I. et. al., (2017) Human neural stem cell-derived cultures in three-dimensional substrates form spontaneously functional neuronal networks. J Tissue Eng Regen Med 2017; 11: 1022-1033.

Still another example is providing unnatural or unnecessary growth factors to stem cells or depriving specific stem cells from growth factors they normally need to best maintain their properties to grow, self-renew and differentiate. Cohen S B et. al., showed that cord blood stem cells are more naïve to their environment and cord blood serum lacks a T cell activation factor. Cohen S B, Perez-Cruz I, Fallen P, Gluckman E, Madrigal J A. 1999. Analysis of the cytokine production by cord and adult blood. Hum. Immunol. 60: 331. De Waele M et. al., also showed that normal cord blood CD34 positive cells, a subset of which is considered to contain the blood stem cell pool, have a growth factor receptor profile and sensitivity to growth factors different than cells found in normal bone marrow or mobilized peripheral blood. De Waele M. et. al., (2004) Growth factor receptor profile of CD34+ cells in normal bone marrow, cord blood and mobilized peripheral blood. Eur J Haematol. Mar;72(3):193-202. Hence, it is important to subject cells to their natural environment if one needs to control the therapy and harness the optimal regenerative product. Sisakhtnezhad S. et. al., (2017) External factors influencing mesenchymal stem cell fate in vitro. European Journal of Cell Biology 96 (2017) 13-33.

Young stem cells have a greater ability to grow and differentiate and a greater stability in culture as compared to adult mature sources of stem cells. Therefore, cord blood from neonates is expected to be a more effective stem cell source than bone marrow. On the other hand, umbilical cord tissue also contains cells and their secretions, is available in limited supply, and there can be variability between neonates. Sharpless N. E. and De Pinho R. A., (2007) "How stem cells age and why this makes us grow old", Nature Rev. Mol. Cell Biol.; Shu S. et. al., (2012), "Immunogenicity of allogeneic mesenchymal stem cells" J. Cell. Mol. Med. Vol 16, No 9, pp. 2094-2103; Lo Sardo, V. et al. (2017) Influence of donor age on induced pluripotent stem cells. Nat. Biotechnol. 35, 69-74.

Some umbilical cord tissue-derived cells are characterized and some are uncharacterized. Those cord tissue-derived cells that are characterized today are defined as "mesenchymal stem cells" or MSCs usually grown using suboptimal unnatural cell culture or harsh processing methods. For example, methods of isolating cells from cord tissue include the use of non-specific enzymes such as proteases that alter cell surface proteins and possibly biology of the cells. Furthermore, the International Society for Cellular Therapy (ISCT) defined MSCs based on methods using high oxygen pressure, incompatible serum, and a cell property that attaches to two-dimensional cell culture environment. Consequently, living products like MSCs are defined by their suboptimal manufacturing methods and cannot provide optimal therapeutic outcomes. In addition, cells that do not attach to conventional two-dimensional surfaces or are uncharacterized because of their small size or number are lost. Mendicino M. et. al., (2014) "MSC-Based Product Characterization for Clinical Trials: An FDA Perspective", Cell Stem Cell 14, Feb 6; Shuvalova N. S. et. al., (2013), "Maintenance of mesenchymal stem cells culture due to the cells with reduced attachment rate" Biopolymers and Cell. Vol. 29. N 1. P. 75-78.

In addition, for stem cells and supportive matrices to be used in tissue engineering and regenerative medicine one must consider two things—safety and efficacy. The method of preparation of cells and tissues for transplantations is very important because manipulating cells and tissue and introducing them to new agents, reagents and environments may turn these cells harmful or inefficient when transplanted in any individual, self or not. Further, current culture methods change stem cells in ways that can reduce or eliminate their efficacy and compromise their safety. Indeed, cord blood transplantation professionals have already complained about quality of cord blood units they receive from public or private banks stating that these low quality cord blood units pose a great risk on patients receiving them. In fact, public banking standards for cord blood collection, diagnosis, processing, banking and releasing have not been established and mandated until October 2011. Excepting bone marrow and cord blood, all other cellular products remain in experimental stage and there are currently no non-blood stem cell FDA processing standards in place. fda.gov/biologicsbloodvaccines/scienceresearch/biologics-researchareas/ucm127182.htm Methods to collect and preserve all types of stem cells fall into two basic categories—unmanipulated (or least minimally manipulated) and manipulated methods.

The minimal manipulation method of collecting and freezing is mainly used for bone marrow and cord blood. The first minimal manipulation involved the collection of blood and direct infusion into a patient. Alternatively, aspirates of blood or marrow were mixed with blood anticoagulant and layered on specific density solutions like Ficoll-Hypaque to allow the density dependent separation of blood mononuclear cells (buffy coat) from plasma and red blood cells. The middle "buffy coat" layer containing the blood (and other) stem cells is gently aspirated, leaving behind the top plasma layer and the bottom layer containing red blood cells. At this stage, the buffy coat is mixed with a cryoprotectant, like dimethyl sulfoxide (DMSO), ethylene glycol or glycerol, to a final concentration of 1% to 10% and immediately slow frozen to −120° C. before immersing it in the liquid or gas phase of a liquid nitrogen storage tank or Dewar. A new version of this method involves replacing the density solution with a set of processing bags connected through tubings and placed in a special device such as the AXP or SEPAX, which are automated closed systems that harvest the stem cell-rich buffy coat containing mononuclear cells from umbilical cord blood. The system reduces a unit of cord blood to a precise volume selected by the operator and does so with high precision and safety.

In other minimal manipulation methods, tissues are excised from one area of the body and retransplanted back in another of the same type. For example, skin from the leg area transplanted in an injured or burnt skin in the arm or face. Another example is scraped or shaved bone from the pelvis transplanted in a fractured or missing bone in the jaw.

The manipulated methods involve manipulating the cells longer than one hour and/or mixing the cells with agents other than water, phosphate buffer solution, cryoprotectant and Ficoll-Hypaque. Typically, in these methods, mechanical sectioning and/or enzymatic digestion of tissue to separate cells is used. Cells may be sorted, transfected for gene therapy and cultured in serum free media or media containing animal or genetically non-identical human sera, or genetically non-identical platelet lysates. Growth factors like epidermal growth factor and hormones like insulin may also be added to stimulate growth and proliferation of cultured cells. Furthermore, cells may be cultured in a two-dimensional or three-dimensional matrix where they may be guided to grow into a specific form. Alternatively, a piece of extracted tissue may be decellularized to create a matrix in which autologous or allogeneic cells may be infused. The matrix containing the necessary cells can be transplanted back into a patient to regrow and heal a degenerated tissue. These methods have a higher risk of negatively impacting stem cell safety and efficacy. Shakouri-Motlagh A. et. al., (2017) Native and solubilized decellularized extracellular matrix: A critical assessment of their potential for improving the expansion of mesenchymal stem cells. Acta Biomaterialia 55 (2017) 1-12; Meral Beksac (2016) How to Improve Cord Blood Transplantation. By Enhancing Cell Count or Engraftment? Frontiers in Medicine, Vol. 3, Article 20; Gentile P. et. al., (2017) Concise Review: The Use of Adipose-Derived Stromal Vascular Fraction Cells and Platelet Rich Plasma in Regenerative Plastic Surgery. Stem Cells; 35:117-134; Smith I. et. al., (2017) Human neural stem cell-derived cultures in three-dimensional substrates form spontaneously functional neuronal networks. J Tissue Eng Regen Med 2017; 11: 1022-1033; Sisakhtnezhad S. et. al., (2017) External factors influencing mesenchymal stem cell fate in vitro. European Journal of Cell Biology 96 (2017) 13-33.

What is needed in the art are better methods isolating, culturing and preserving stem cells and compatible biomatrices that provides more reliable, reproducible, safer and efficacious products.

BRIEF SUMMARY OF THE INVENTION

The present disclosure describes a method of collection and a four way processing of human umbilical cord to manufacture four products: 1) Autologous or HLA- and optionally gender-matched plasma and red blood cell-reduced cord blood for transplantation in an autologous, related or unrelated patient; 2) Autologous or HLA- and optionally gender matched serum, plasma, or platelet lysate, for use in culturing cells; 3) A complete mixture of autologous or HLA- and optionally gender-matched cells liberated from a portion of intact cord tissue; 4) An autologous or HLA- and optionally gender-matched decellularized tissue matrix prepared from an intact portion of cord tissue, which can be cut into desired shapes or left as a slurry of small matrix fragments; 5) A combination of 3 and 4, wherein the mixture of cells is reinfused back into the decellularized tissue matrix. Any combination of products 1-5 is possible, and each of the products can be used as is, stored by e.g., freezing, or cultured to amplify cells, or any combination therein.

In addition, methods of producing stem cell products for research and therapies are provided. For example, a complete cell mixture liberated from intact cord tissue can be infused back into the decellularized tissue matrix and subsequently cultured in three dimensions (3D) in media containing autologous serum, plasma or platelet lysate in the presence of low oxygen tension. This methodology produces well-preserved cell and biomatrix products with better regenerative potential for injured, diseased and aging patients or animals.

In more detail, the disclosure is a method of producing stem cells and tissue matrix. Preferably, the tissue preparation commences within 48 hours, preferably within 16 or 12 hours, of obtaining the tissue, and the process occurs in at least a class 10,000 clean room facility.

The method begins with obtaining (directly or indirectly) cord tissue from a newborn animal. The tissue will be sterilized then cut into two or more portions. A portion of the tissue is used to prepare decellularized matrix from whole cord tissue that can function as a three dimensional matrix for subsequent cell culturing or tissue engineering techniques. Another portion of the same whole cord tissue is used to collect all cells within this whole cord tissue.

For decellularized matrix, the tissue is used as whole or cut into desired fragments shapes before being chemically, enzymatically and/or mechanically treated to liberate cells or cellular debris, leaving a decellularized tissue matrix from which at least 70%, preferably 75%, 80%, 85%, 90% or 95%, of the cells have been removed. Although any method of decellularization can be used, we prefer methods that avoid the use of enzymes or harsh chemicals.

It is usually preferred that the vessels of the tissue not be separated from the rest of the tissue, because the tissue with vessels may be important and necessary for tissue engineering and proper three-dimensional cell culturing conditions.

For decellularized matrix, the tissue can be shaped before decellularization, after decellularization, or both, but decellularization is easier with greater surface area, so it is preferred that the tissue is somewhat cut or shaped before decellularization. A piece of cord tissue can thus be minced, or cut into flat slices or blocks, or spiral cut, or any other desired way so as to create a gel or slurry of small fragments, sheets, blocks, or rolls of material having different thicknesses, lengths and widths ranging from micrometers to meters. These shapes are chosen according to the intended use of the decellularized matrix material, e.g., a large sheet being suitable for burned skin replacement.

For decellularized matrix, it may be preferred that the fragmentation or cutting is made on cord tissue that is fresh, but it could also be embedded in a biodegradable natural or synthetic polymer or even frozen using for example a fixed or moving blade or laser. Embedding or freezing the cord will aid in e.g., spiral slicing of cord tissue.

A second portion of the tissue is used to obtain all the cells inside the tissue by mechanically dissociating the tissues from the cells. The tissue is gently mechanically dissociated, e.g., with a blade, a laser or homogenizer. Then the tissue fragments are gently agitated to release intact cells. Although any method of liberating cells can be used, we prefer gentle agitation and other methods that avoid the use of enzymes.

The liberated cells will be a complete mixture of all cell types found in the tissue, including, endothelial cells, epithelial cells, mesenchymal cells, adherent and non-adherent cells, mesenchymal stem cells, mesenchymal progenitor cells and others. The goal is to liberate, collect and preserve all cell types in the tissue.

The cells are then cultured and/or directly stored, either atone or with autologous serum and/or decellularized tissue. Cells can also be cultured alone or with autologous serum and/or decellularized tissue. Preferably, they are both stored and cultured with autologous serum, etc., as this provides a better product. Also, preferred they are cultured with decellularized tissue at some point before use, as the decellularized tissue provides a natural matrix for 3D growth.

Culturing is preferably via a three dimensional cell culture in a hypoxic environment at 37° C. in a medium supplemented with autologous or syngeneic serum, plasma or platelet lysate. Preferably, the culturing step is in a humidified carbon dioxide cell culture chamber. The point of culturing the cells in a hypoxic environment is to enhance stem cell self-renewal and differentiation potential. Hypoxic environment and 3D culturing provides a more natural environment, and minimizes the cellular changes that can occur on culturing. Further, the addition of decellularized tissue fragments or shaped decellularized tissue matrix provides an example of 3D environment that more closely mimics the in vivo environment.

The starting tissue can be any tissue from the body that contains some stem cells, and preferably includes skin, umbilical cord, heart, brain, or hair. However, body fluids such as urine, blood and the like can also be used. A preferred tissue is whole umbilical cord tissue, which can contain more or less cord blood.

The decellularized tissue matrix, tissue fragments and the cells can be used immediately or stored for future use, and they can be stored either together or separately, again depending on the ultimate use. Storage can be by freezing, e.g., with a cell protecting agent such as DMSO or glycerol, but the tissue matrix can be freeze dried or lyophilized as well, and rehydrated for use according to known techniques.

Importantly, the method produces a mixture of differentiated cells, stem cells and progenitor cells. These cells can be used as is, or used after first re-infusing back into a decellularized tissue matrix, prepared as described herein. The stem cells can also undergo further separation, amplification and differentiation into a desired cell type, but we specifically contemplate using a mixture of cells in therapeutic applications. The mixture of cells provides a more natural environment, where stem cells can respond to signals from other cells and/or the matrix to stimulate differentiation into the desired cell type.

When used together with a decellularized tissue matrix, that matrix can be from the same or a genetically identical (syngeneic) animal, but it could also be from a different animal, since the matrix is largely decellularized and the matrix itself will be minimally antigenic. The decellularized tissue matrix provides the cells with a scaffold for growth, as well as the needed growth factors and the like, ensuring a highly safe and effective, biocompatible tissue replacement.

Another embodiment is a method of cell therapy, wherein the products described herein are transplanted into a patient. Other embodiments of the disclosure are methods of stem cell therapy, using one or more of the products and/or methods described herein.

In more detail, the invention includes any one or more of the following embodiments, in any combination(s) thereof:

---

A method of producing stem cells and tissue matrix, comprising:
a) obtaining a tissue from an animal source;
b) cleaning said tissue with a sterilizing agent;
c) mechanically dissociating said tissue to produce cells and tissue fragments;
d) mechanically or chemically treating said tissue fragments to produce cells or lysed cells and tissue matrix;
e) culturing said cells in a three dimensional cell culture in hypoxic oxygen environment at 37° C. in a medium supplemented with serum, plasma or platelet lysate isolated from said animal source or a genetically identical animal source, wherein said cells are cultured alone or together with said tissue matrix or said tissue fragments.
Any method herein described, whereby tissue is selected from skin, umbilical cord, heart, brain, or hair.
Any method herein described, whereby i) the tissue matrix and the cells are cultured together and stored together, ii) the tissue matrix and the cells are cultured together and stored separately, iii) the tissue matrix and the cells are cultured separately and stored separately, iv) the tissue fragments and the cells are cultured separately and stored separately; v) the tissue fragments and the cells are cultured together and stored together or vi) the tissue fragments and the cells are cultured together and stored separately.
Any method herein described, whereby said cells are a mixture of differentiated cells, stem cells and progenitor cells.
Any method herein described, whereby steps c-e) commence within 48 hours of said obtaining step.
Any method herein described, wherein said mechanically dissociating step is by slicing or dicing said tissue with a blade.
Any method herein described, wherein said tissue is sliced into a desired shape.
Any method herein described, where said culturing step is in a humidified carbon dioxide cell culture chamber.
Any method herein described, where said tissue matrix and cells are stored together or separately at temperatures between −80° C. and −196° C.
Any method herein described, where said tissue matrix is freeze-dried and stored at −80° C.
Any method herein described, where said freeze-dried tissue matrix is thawed in the presence of phosphate buffer solution or water.
Any method herein described, where said tissue matrix is lyophilized and stored at room temperature.
Any method herein described, where said lyophilized tissue matrix is reconstituted with water or phosphate buffer solution.
Any method herein described, further comprising reintroducing said cells into said tissue matrix before use.
Any method herein described, wherein said cells and said tissue matrix are separated before storage and further comprising reintroducing said cells into a genetically identical or different tissue matrix before use.
A method of producing stem cells comprising:
a) obtaining an umbilical cord from a source;
b) cleaning said umbilical cord with a sterilizing agent;
c) mechanically dissociating said umbilical cord to produce tissue fragments and cells;
d) culturing said tissue fragments and said cells in a three-dimensional cell culture in a hypoxic oxygen environment at 37° C. in a medium; and
e) collecting said cells and said tissue fragments, wherein said cells are a mixture of differentiated cells, stem cells, and progenitor cells.
Any method herein described, wherein said medium is supplemented with serum, plasma or platelet lysate isolated from said source or a genetically identical source.
Any method herein described, wherein said mechanically dissociating is cutting thin slices.
Any method herein described, wherein said cells are reinfused into a tissue matrix before use.
Any method herein described, wherein said tissue matrix is from said source.
Any method herein described, wherein said tissue matrix is from a different source.
A method of preparing a cell mixture of all cell types present in umbilical cord tissue, said cell mixture obtained by the following steps:
a) obtaining a first intact portion of umbilical cord tissue from an umbilical cord of a first newborn animal;
b) cleaning said first intact portion of umbilical cord tissue with a sterilizing agent;

c) mechanically dissociating said first intact portion of umbilical cord tissue into smaller fragments;
d) mechanically liberating cells from said smaller fragments; and
e) collecting a cell mixture of all cells types liberated from said smaller fragments, wherein said cell mixture includes differentiated cells, stem cells and progenitor cells; and
f) combining said cell mixture with autologous or syngeneic or HLA- and gender matched serum, plasma or platelet lysate for culturing or storage, or both.
A method of making biomatrix comprising:
a) obtaining a second intact portion of umbilical cord tissue from said first newborn animal or from a second newborn animal;
b) cutting said second intact portion of umbilical cord tissue to a desired shape without separating vessels from the rest of the cord tissue;
c) decellularizing said second umbilical cord tissue to produce a decellularized tissue;
d) culturing said cell mixture together with said decellularized tissue such that said decellularized tissue provides a 3D scaffold for 3D culturing of said cells mixture, wherein said 3D culturing is in a 0.1%
to 5% or 0.5-7% oxygen environment at 37° C. in a medium supplemented with autologous or syngeneic or HLA- and gender-matched serum, plasma or platelet lysate.
Any method herein described, wherein said cell mixture comprises about 10% of non-adhering pluripotent cells, 40% of adhering pluripotent stem cells, and 50% of differentiated cells, wherein cells in the cell mixture having sizes ranging from 3-100 μm in diameter.
Any method herein described, wherein said decellularized tissue is from said first newborn animal.
Any method herein described, further comprising adding mononuclear cells obtained from the umbilical cord blood from said first newborn animal to the cell mixture being cultured.
Any method herein described, wherein said culturing is under 0.5% to 7% oxygen.
Any method herein described, wherein said medium is supplemented with umbilical cord plasma obtained from umbilical cord blood from the first newborn animal.
Any method herein described, further comprising adding mononuclear cells obtained from the umbilical cord blood from the first newborn animal to said culture.
Any method herein described, wherein said culturing is under 0.5% to 7% oxygen.
Any method herein described, further comprising adding mononuclear cells obtained from the umbilical cord blood from the first newborn animal to said cell mixture.
Any method herein described, wherein said cell mixture is cultured under 0.5% to 7% oxygen.
Any method herein described, wherein the cell mixture being cultured under 0.5% to 7% oxygen in a medium supplemented with umbilical cord plasma obtained from umbilical cord blood from the first newborn animal.
A decellularized tissue biomatrix, said biomatrix being obtained by the following steps:
a) obtaining a first intact portion of umbilical cord tissue from the umbilical cord of a first newborn animal;
b) cleaning said first intact portion of umbilical cord tissue with a sterilizing agent;
c) cutting said first intact portion of umbilical cord tissue to a desired shape without separating vessels from the rest of the cord tissue and decellularizing said first intact portion of umbilical cord tissue to produce decellularized tissue; and
d) optionally further mechanically changing the size or shape or both of the decellularized tissue to obtain said biomatrix.
Any method herein described, wherein the biomatrix is combined with a mixture of cells isolated from a second intact portion of cord tissue from said newborn animal or a second newborn animal
Any method herein described, wherein said combination is cultured under 0.5% to 7% oxygen.
Any method herein described, wherein said combination is cultured under 0.5% to 7% oxygen in a medium supplemented with umbilical cord plasma obtained from umbilical cord blood from said first newborn animal.
Any method herein described, wherein said combination is cultured under 0.5% to 7% oxygen in a medium supplemented with autologous, syngeneic or HLA matched plasma, serum or platelet lysate.
Any method herein described, said biomatrix being stored at temperatures between −80° C. and −196° C.
Any method herein described, said biomatrix being lyophilized and stored at −80° C.
Any method herein described, said biomatrix being lyophilized and stored at room temperature.
Any method herein described, where the lyophilized acellular biomatrix is reconstituted with water or phosphate buffer solution.
Any method herein described, where the lyophilized acellular biomatrix is reconstituted with water or phosphate buffer solution.
Any product herein described, wherein one or more of i) said cell mixture or ii) said serum, plasma or platelet lysate or iii) said decellularized tissue is a pooled HLA-matched product, each pooled portion of said HLA-matched product having the same at least 3 matched MHC loci.
A method of culturing stem cells, said method comprising:
a) obtaining stem cells from a first donor;
b) obtaining sera from an HLA- and gender matched second donor having the same gender and at least 3 HLA types that are the same as said first donor; and
c) culturing said stems cells in a medium supplemented with 1-10% of said sera.
A method of culturing stem cells, said method comprising:
a) obtaining stem cells;
b) obtaining plasma, serum or platelet lysate that is HLA-matched and optionally gender matched to said stem cells and having at least 3 MHC loci that are matched to said stem cells; and
c) culturing said stems cells under hypoxic (0.1-7% $O_2$) conditions in a medium supplemented with 1-10% of said plasma, serum or platelet lysate
A stem cell product for use in a stem cell treatment of a patient, said product comprising a cell mixture of all cell types cells from umbilical cord tissue that is cultured in a 3D scaffold made from an intact portion of decellularized cord tissue under hypoxic conditions in a media supplemented with 1-10% serum, plasma or platelet lysate, wherein said cell mixture and said serum, plasma or platelet lysate are from a same donor and where said donor has at least 3 HLA matches with a patient to be treated with said product. Preferably, the decellularized tissue matrix is also from the same source, although this is not essential.

A stem cell product for use in a stem cell treatment of a patient, said product comprising a cell mixture of all cell types cells mechanically from comminuted umbilical cord tissue that is cultured in a 3D scaffold made from an intact portion of decellularized cord tissue under hypoxic conditions in a media supplemented with 1-10% serum, plasma or platelet lysate, wherein said cell mixture and said serum, plasma or platelet lysate are from a same donor and where said donor has at least 3 MHC loci matched with a patient to be treated with said product. Most preferred, the donor IS the patient. Preferably, the decellularized tissue matrix is also from the same source, although this is not essential.

A regenerative medicine product for use in treatment of a patient, said product comprising a cell mixture of cell types liberated from umbilical cord tissue, wherein said cell mixture is cultured in a 3D scaffold made from an intact portion of decellularized cord tissue under hypoxic conditions in a media supplemented with 1-10% serum, plasma or platelet lysate, wherein said cell mixture, decellularized cord tissue and said serum, plasma or platelet lysate have the same at least 3 MHC loci matched with a patient to be treated with said product.

A stem cell product for use in a stem cell treatment of a patient, said product comprising a cell mixture of cell types mechanically released from comminuted umbilical cord tissue that is cultured in a 3D scaffold made from an intact portion of decellularized cord tissue under hypoxic conditions in a media supplemented with 1-10% serum, plasma or platelet lysate, wherein said cell mixture, said decellularized cord tissue and said serum, plasma or platelet lysate each have the same at least 3 MHC loci matched with a patient to be treated with said product.

Preferably, all combination products here come from the same source and are thus autologous. However, where material is limiting, any one or more of the various components can be HLA matched, so long as the same 3 HLA matching loci are present in all heterologous components. Ideally, where components are pooled, the same donors provide all pooled portions, thus minimizing the variability in products.

A product comprising mixed cells on a biomatrix scaffold, each as described herein, that is 3D hypoxically cultured with serum, plasma or platelet lysate, as described herein. Such products can be further combined with mononuclear cells from cord blood or with other products.

---

There are substantial differences between the disclosure as described and claimed herein and the prior art methodologies. These are elaborated on below.

The facility in which the procedure is executed should be a dedicated clean room with positive air-flow. The clean room facility is made of at least three zones, the actual clean room where processing occurs (preferably class 10,000 (Iso 4) or better), as well as a gowning room (preferably class 10,000 or better), and an entry airlock room (preferably class 10,000 or better). Preferably, the facility also has sample receiving rooms, diagnostic rooms (for performing tests for infectious disease, and the like) and final sample storage rooms, as well as pass-through hatches for samples to pass to each next processing zone.

By "class 10,000 compliant," what is meant that the facility at least complies with the US FED STD 209E regulations or equivalent. Also, preferably the facility is a dual process facility, with separate but mirrored facilities for public and private stem cell processing and banking facilities. A preferred facility is described in U.S. Pat. No. 8,656,670, filed Jul. 22, 2012, and incorporated herein by reference in its entirety.

Following expectant mother screening and her consent, cord blood is collected aseptically after the baby is born vaginally or by C-section and separated from the mother. While the placenta is still in utero or removed, cord blood is collected using a needle inserted in the umbilical vein that allows blood to drain into a bag containing anti-coagulant like Citrate Phosphate Dextrose (CPD), EDTA or heparin.

Following blood collection, whole cord tissue is collected, rinsed from blood and sterilized before it is placed in another collection bag. Blood and tissue bags are each doubly wrapped and placed in different temperature controlled compartments of a shipping container, sealed and immediately shipped to our hybrid tissue bank for diagnostics, processing and banking.

In a clean room, cord blood is transferred to an AXP® (Cesca Therapeutics) or SEPAX® (Biosafe) processing bag, then the blood is differentially centrifuged to separate it into three products: a plasma and red blood cell reduced cord blood bag, a plasma bag and a red blood cell bag. Then, each of plasma, red blood cell and blood stem cell bags are separated. Cord blood plasma bag is aliquoted into different sterile tubes or vials wrapped and saved at temperatures between −196° C. and 4° C.

The blood stem cell bag is infused with a cryoprotectant like DMSO, ethylene or propylene glycol and an additive, then slowly or snap frozen to −196° C. and banked in 24/7 monitored dewars. On the other hand, whole cord tissue is transported at 0° C. to 8° C. to our hybrid tissue bank. The whole cord is cut into two or more pieces. Some of the pieces are used to collect all cells from the tissue of the cord. The rest of cord pieces are used to produce a decellularized cord tissue matrix.

From each cord the following individual products are isolated: i) cord blood, ii) cord blood plasma and related products, iii) cord tissue derived cells and iv) cord tissue derived decellularized tissue matrix, and v) combinations thereof.

The method uses the whole tissue to produce cell mixtures and decellularized tissue matrix, after emptying cord tissue from cord blood and collecting the blood in a bag, although of course cord tissue may contain some amount of remaining blood.

The tissue is CUT to a certain shape (without separating vessels from rest of tissue) before or after (or both) producing a decellularized tissue matrix of the desired shape, devoid of cells, with or preferably without using nucleases or other enzymes, as described in US20050203636, U.S. Pat. Nos. 7,775,965, and 7,318,998.

In the initial isolation and freezing or culturing, the method is not focused on specific cell types (such as mesenchymal stem cells or endothelial stem cells), nor on using 2D cell cultures and fetal bovine serum supplementation, as described in US20110129918, US20060223177. Instead, the cells are isolated as a mixture of different cell types and frozen or cultured in 3D as a suspension or on 3D surfaces, preferably a 3D decellularized tissue matrix derived from the same or another newborn, again providing a more natural culture environment.

Preferably, we use autologous or syngeneic serum and other products, prepared from the cord blood and also from blood donated by the same individual later in life. The cord blood is only present in small quantities, and thus has previously not been used in this way. However, we have discovered that there is enough cord blood for an initial short culture and/or storage of the cord cell mixture, and when the cells are later needed for treatment, the individual can provide additional blood for further culture.

Serum and platelets contain natural amounts of growth factors and cytokines necessary to maintain cells and stem cells in their natural cross talk environment being either an undifferentiated state or a state of response to differentiation factors. In addition to making the product more potent, using autologous or syngeneic blood and tissue components and reducing foreign agents in cell culture media during biological preparations like stem cell processing is more accepted by the scientific community. More importantly it may eventually reduce the time to market these newborn derived products by facilitating FDA approval and hence patients may benefit more quickly.

As another option, given the small amount of cord blood available (Wagner J E. et. al., (2002) "Transplantation of unrelated donor umbilical cord blood in 102 patients with malignant and nonmalignant diseases: influence of CD34 cell dose and HLA disparity on treatment-related mortality and survival". Blood, 100:1611-1618), HLA typed blood and cells could be used, including pooled products with at least 3 MHC loci that are the same, and that where pooled products are used they each have the same matched loci. The human leukocyte antigen (HLA) system or complex is a gene complex encoding the major histocompatibility complex (MHC) proteins in humans. These cell surface proteins are responsible for the regulation of the immune system in humans. HLA genes are highly polymorphic, which means that they have many different alleles, allowing them to fine-tune the adaptive immune system.

Given the small amount of cord tissue cells and decellularized matrix available, we also envisage using cord blood, cord tissue-derived cells and cord tissue-derived decellularized cord tissue matrix that are matched at HLA loci and optionally gender matched to help transplant patients who do not have their own normal cord blood and cord tissue saved. Specifically, we can produce one or more combinations of cord blood, cord tissue cells, cord tissue matrix and cord blood sera, plasma and platelets lysates where one or more of these products are derived from the same HLA- and optionally sex matched donors, such that the pooled and combination products all have the same at least 3 matched MHC loci. Although such HLA-matched products are ideally taken from HLA-matched cords, they can also be taken from HLA-matched adults.

We also allow pooling of cord blood products, cord tissue cell products, decellularized matrix products and combinations thereof, but each of the donor sources should have same at least 3 matched MHC loci, so that all pooled and combination products ideally all have the same 3 MHC loci, which also matches to patient in which the various products are to be used. Combination products can also include combinations of autologous and these HLA matched components.

The purpose of this matching is to minimize immunoreactivity between the cells, matrix and serum/plasma/platelets products when cultured together. It also minimizes rejection and improves transplant outcome when these products are transplanted in an HLA-matched patient. Hence, unlike current practice, a pool of allogeneic normal cord blood, sera or plasma, cord tissue cells and cord tissue matrix that are gender specific and/or matched at HLA loci will significantly help transplant patients who do not have their own normal cord blood, serum or plasma, cord tissue cells and cord matrix saved. McNiece I. et. al., (2004) "Ex vivo expansion of umbilical cord blood hemopoietic stem and progenitor cells". Exp Hematol., 32:409-413.

The cells are grown in 3D (e.g., in a mini bioreactor). Three dimensional culture techniques have been applied to stem cell culturing. However, culturing or co-culturing cells in a bioreactor, in or on a three dimensional surface derived from the same or similar genetic source is novel and is expected to improved biological properties. When it comes to stem cells, it is important to preserve their differentiation potential in response to stimuli. 3D culturing on matrices or scaffold derived from the same cell source is expected to enhance the usefulness of the cells when transplanted alone or when transplanted in combination with the matrix or scaffold. The transplanted matrix or scaffold provides cells with a surface that is appropriate for their migration, proliferation or differentiation on or within the matrix.

Stem cells are also cultured in a hypoxic environment. Currently transplanted cells are cultured under atmospheric oxygen pressure. Herein, by contrast, we use cells that are gradually or suddenly exposed to a hypoxic environment ranging from 0.5% to 7% oxygen while cultured in or on a 3D matrix in the presence or absence of 1% to 10% autologous blood components in an incubator at 37° C. for e.g., 1-7 days, or up to 2 or 3 weeks, or more. These conditions produce a novel biologically active cellular product that is more useful for regenerative medicine.

The cell mixture liberated from cord tissue is reinfused into the acellular tissue matrix. Cells are reinfused at a specific density of 50,000 to 600,000 cells per cubic centimeter of a piece of vascularized or avascularized tissue that has been decellularized. For cell combinations, for example a 5 to 1 ratio of mesenchymal stem cells to endothelial progenitor cells are infused in a decellularized piece of cord tissue and incubated under conditions mentioned above. Alternatively, stem cells can be stimulated to differentiate into a desired cell type, like a muscle, cartilage, bone or skin cell, prior to infusing them at a specific density of 50,000 to $10^7$ cells per cubic centimeter of decellularized matrix.

By "animal" herein what is meant is any non-human animal or human. Preferably the animals are mammals.

By "medium" herein what is meant is phosphate buffer saline (PBS) or chemically defined medium.

By "decellularized cord tissue-derived matrix" herein what is meant is that at least 70% of the original cells of said tissue have been removed, leaving behind a native extracellular matrix (ECM) containing connective tissue, proteoglycans, such as heparin sulfate, chondroitin sulfate, and keratin sulfate, non-proteoglycan polysaccharides, such as hyaluronic acid, fibers such as collagen and elastin, and miscellaneous components such as fibronectin, laminin and vitronectin. This product is not the same as ECM that is secreted by cells grown in culture, but has a more natural structure since it originated from natural tissue, rather than by cells grown in culture.

By "hypoxic" what is meant herein is that the cells are cultured in low oxygen tension with less than usual pressure of 159 mm Hg (21% $O_2$), but are not anoxic. Preferably, 0.1-15% $O_2$ is used, preferably or 0.5-7% or 0.5-5%, or 1-5% $O_2$ for cells from the umbilical cord.

By "mechanically dissociating" what is meant is physical method of reducing tissue size, e.g., by slicing or cutting, triturating or homogenizing, mortar and pestle, and the like. Preferably, the tissue is cut into fine strips or cubes with a blade.

By "mechanically liberating" what is meant are physical methods of gently liberating cells from tissue, such as gentle homogenization or rocking on a rocker plate or passing a slow flow over the tissue, and the like.

By "HLA-matched" what is meant is cells or blood products are from HLA-matched donors, wherein at least three (3) major histocompatibility complex (MHC) genes match. When there is 100% genetic matching of ALL MHC genes, the materials are autologous. Pooled and combination products from pooled resources should also have the same 3 HLA matched loci.

By "matched" here, we refer to the recipient as the genome against which loci are matched. Thus, HLA-matched products must have at least 3 MHC loci that match the patient where the product is to be used.

As used herein, "intact portion" means the cord tissue is used as is, and the vessels are not dissected out for separate use, although the cord itself can be halved or cut into thirds, or comminuted, etc.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise," "have," "include" and "contain" (and their variants) are open-ended linking verbs and allow the addition of other elements when used in a claim.

The phrase "consisting of" is a closed linking verb and does not allow the addition of any other elements.

The phrase "consisting essentially of" occupies a middle ground, allowing the addition of non-material elements such as extra washes, precipitations, drying or various buffers and the like.

The following abbreviations are used herein:

| | |
|---|---|
| GMP | Good Manufacturing Practices |
| FDA | Food and Drug Administration |
| DMSO | Dimethylsulfoxide |
| DMEM | Dulbecco Modified Essential Medium |
| SCR | Stem Cell Reserve |
| PAA | Peracetic Acid |

BRIEF DESCRIPTION OF THE DRAWINGS

FIG. 4A-I are illustrations of mechanical dissociation of umbilical cord tissues to produce decellularized matrices. This figure shows how an intact whole umbilical cord devoid of blood is sliced, cut or comminuted before or after decellularization.

Figure 1:
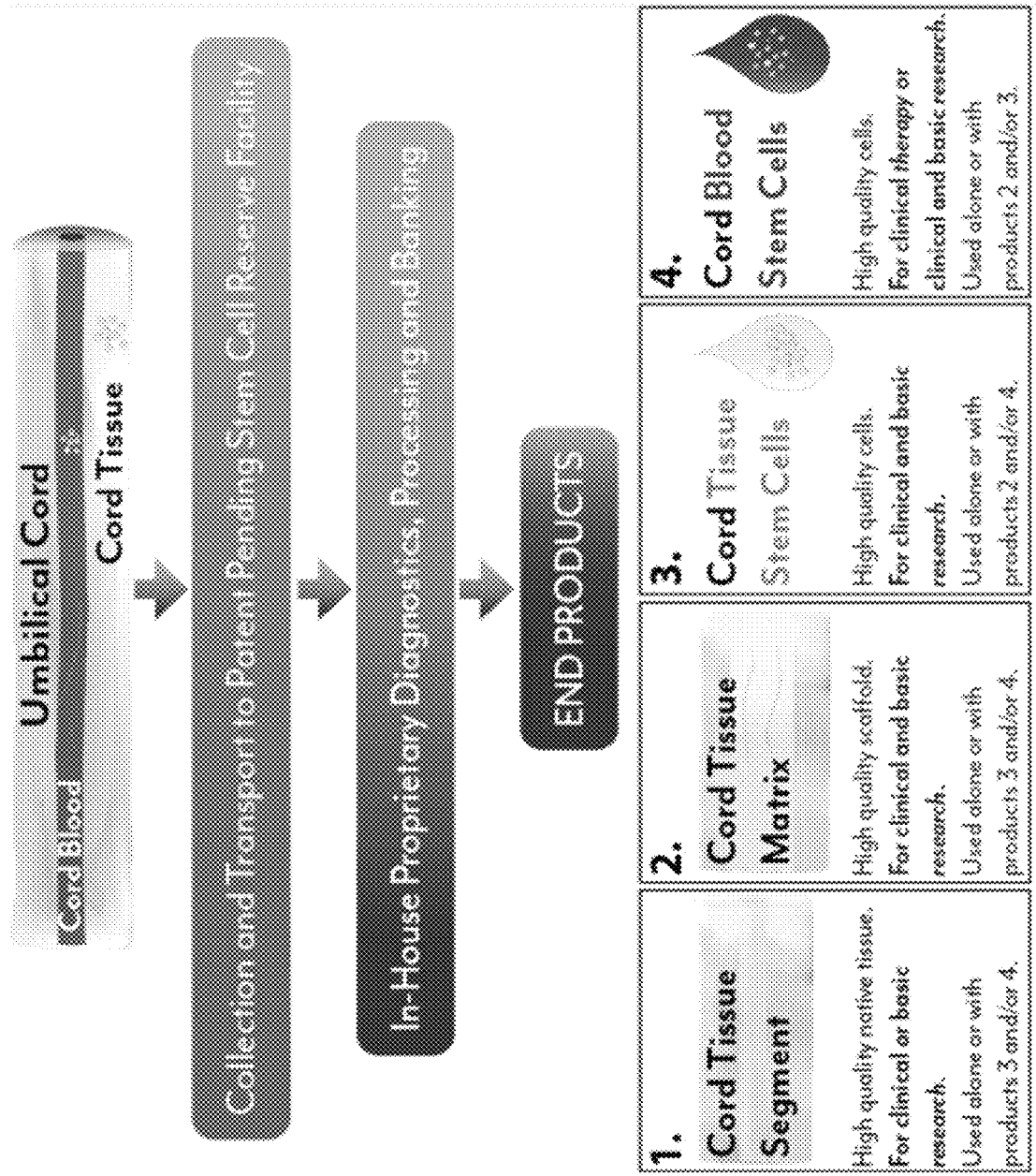
FIG. 1 shows some of the products derived from each umbilical cord and their use singly or in combination with other products derived from the same umbilical cord.

TABLE 1 shows the possible combination of 100% genetically compatible serum, plasma or platelet lysate as well as cord blood and cord tissue-derived cells and matrix from newborn A before or after culturing at 37° C. in low oxygen tension and before using for research or transplanting in same patient A, or an HLA- and optionally sex-matched patient.

TABLE 2 shows the possible combination of 100% genetically compatible serum, plasma or platelet lysate as well as cord blood and cord tissue-derived cells from newborn A with or without a pooled HLA- and optionally sex-matched cord tissue-derived matrix from a different newborn before or after culturing at 37° C. in low oxygen tension and before using for research or transplanting in same patient A or an HLA- and optionally sex-matched patient.

TABLE 3 shows the possible combination of 100% genetically compatible cord blood and cord tissue-derived cells and matrix from newborn A cultured in the presence or absence of pooled HLA- and optionally sex-matched blood sera, plasmas or platelet lysates before or after culturing at 37° C. in low oxygen tension and before using for research or transplanting in same patient A or an HLA- and optionally sex-matched patient.

TABLE 4 shows the possible combination of 100% genetically compatible cord blood and cord tissue-derived cells from newborn A cultured in the presence or absence of pooled HLA- and optionally sex-matched blood sera, plasmas or platelet lysates with or without pooled HLA- and optionally sex-matched cord tissue-derived matrix from the same pool of donors before or after culturing at 37° C. in low oxygen tension and before using for research or transplanting in same patient A, or an HLA- and optionally sex-matched patient.

TABLE 5 lists various unlimiting embodiments of the invention, showing the possible mix of products of HLA- and optionally sex matched cord blood units, HLA- and optionally sex matched cord blood units cord tissue-derived cells, HLA- and optionally sex matched cord blood units blood sera, plasmas or platelet lysates and HLA- and optionally sex matched cord blood units cord tissue-derived matrices all derived from the same pool of donors before or after 3D culture at 37° C. in low oxygen tension and delivery to research or transplanting in an HLA- and optionally sex matched patient.

DETAILED DESCRIPTION OF THE INVENTION

The present disclosure provides any one or more of the following embodiments, in any combination: 1) 3D culture expanded cord blood in the presence of autologous cord tissue-derived cells and plasma; 2) 3D culture expanded cord blood in the presence of autologous cord tissue-derived matrix and plasma; 3) 3D culture expanded cord blood in the presence of autologous cord tissue-derived cells, cord tissue-derived matrix and plasma; 4) cord blood sera and other products for use in storage and culturing of cells; 5) umbilical cord tissue-derived biomatrix, which is decellularized cord tissue with intact or broken vessels; 6) umbilical cord tissue-derived cells, which is a complete mixture of cells mechanically liberated from the cord tissue; 7) a mixture of 5 and 6, where the mix of cord tissue cells are reinfused back into the decellularized tissue, 8) a mixture of cord blood mixed with autologous 5 and 6, where the mix of cord tissue cells are reinfused back into the decellularized tissue.

In any of the above, the cells can be amplified in culture before use, and the amplification can occur before storage or after storage (or both), and occur before combining the matrix with the cell or after such combination, or combinations thereof. Preferably, the cells are both stored and cultured with autologous or syngeneic serum and similar products, although HLA and gender matched serum and similar products can be used as well.

Furthermore, the decellularized cord tissue can be used with any other stem cells, and are not limited to use with the cord tissue mixture of cells. Thus, they can be used with stem cells from cord blood, mixed cells from cord blood, adult stem cells from bone marrow, epithelia, adipose tissue, and the like. As yet another alternative, the mixture of cells can be combined with other cell types for use.

Additional products may comprise the following, as seen in Tables 1 through 5: umbilical cord blood cells and umbilical cord tissue-derived cells, preserved hypoxia conditioned whole umbilical cord tissue-derived matrix cultured in 0.5%-7% or 0.5%-5% oxygen tension in the presence or absence of 100% genetically compatible cord blood plasma, 100% compatible umbilical cord tissue-derived matrix and cells cultured in 0.5%-7% oxygen tension in the presence of 100% genetically compatible cord blood plasma; 100% compatible umbilical cord tissue-derived matrix and umbilical cord blood mononuclear cells cultured in 0.5%-7% oxygen tension in the presence of 100% genetically compatible cord blood plasma, 100% compatible umbilical cord tissue-derived matrix and cells and umbilical cord blood mononuclear cells cultured in 0.5%-7% oxygen tension in the presence of 100% compatible cord blood plasma, 100% compatible umbilical cord blood mononuclear cells and umbilical cord tissue-derived cells cultured in 0.5%-7% oxygen tension in the presence or absence of cord blood plasma, and umbilical cord tissue-derived cells cultured in 0.5%-7% oxygen tension in the presence or absence of cord blood plasma. The products of this disclosure also include pooled HLA- and optionally sex matched cord tissue-derived cells, pooled HLA- and optionally sex matched sera, plasmas or platelet lysates obtained from pooled HLA- and optionally sex-matched blood units, HLA- and optionally sex matched whole umbilical cord tissue matrix obtained from pooled HLA- and optionally sex-matched umbilical cord tissues and the combination of these products before and after 3D culturing.

Cord blood and cord tissue are collected and the cord blood separated from the tissue as much as possible. The cord blood is typically collected in anticoagulant supplemented bag then mononuclear cells or buffy coat are separated as much as possible by centrifugation from red blood cells and plasma using common blood processing techniques like Ficoll Hypaque density gradient centrifugation or the "closed technique" using AXP AutoExpress from Cesca Therapeutics or Sepax from Biosafe. Consequently, cord blood products are a bag of cord blood containing mononuclear cells made of hematopoietic lineage cells such as lymphocytes, monocytes, stem and progenitor cells as well as mesenchymal stromal cells.

Cord blood processing also produces a bag of red blood cell concentrate and another bag of plasma. Serum can also be collected from coagulated cord blood that is centrifuged at 200-800 g for 5-20 min to sediment all cells. Serum is blood without fibrinogen. It contains salt, water, antibodies, non-clotting proteins like growth factors and antigens although some clotting proteins remain. It is used right away for culturing cells or immunotherapy or for cryostoring biological products. Plasma is the liquid constituent of blood when it is not coagulated. It contains salt, water, antibodies, proteins, clotting factors and antigens. Plasma is derived from anticoagulated blood that is centrifuged at 200-800 g for 5-20 min to remove blood cells. Plasma also has a higher level of proteins than serum because during serum manufacturing some proteins get lost during coagulation and sedimentation. Plasma is useful as a source of growth factors for cell culture and for cell and tissue storage. It is also useful to treat people suffering from burns, shock, trauma, and other medical emergencies. The proteins and antibodies in plasma are also used to create therapies for rare chronic conditions, such as autoimmune disorders and hemophilia.

Platelets are non-nucleated fragments of mature megakaryocytes. There are several centrifugation protocols to collect platelets from anticoagulated blood. One example is to spin anticoagulated blood at 300 g for 5 min at 12° C. followed by collecting the supernatant and spinning at 700 g for 17 min. The resulting pellet contains platelets and some red and white blood cell impurities. Most plasma supernatant is removed and enough is left to resuspend the platelets. Platelets are essential for blood clotting however they also contain valuable growth factors useful for cell culture, proliferation and survival. To release these factors, platelets should be lysed. There are several ways to lyse platelets. One example is by repeated cycles of freezing at −80° C. for hours and thawing at 37° C. To remove platelets membranes, the lysate is spun at 4,000 rpm for 30 min at room temperature in a centrifuge and the supernatant is transferred to another sterile tube. Serum, plasma, platelets lysate can be used right away or stored, and typically will be used right away to culture and store the other products.

The cord tissue is cleaned and cut into two portions, or it can be cut into portions first. The first portion is for the purpose of collecting all the cells inside the umbilical cord, and the second one for the purpose of obtaining a decellularized matrix. As one alternative, we could also use the same piece for both processes, when we mince the tissue or slice it fine enough to liberate the cells with gentle agitation. However, typically we use different portions for the two products.

The sterilizing agent can be selected from those known in the field, including hydrogen peroxide, isopropyl alcohol, ethanol or CholaPrep™ from Becton Dickinson.

In order to make a cell mixture, the cord is typically minced, although thin slices could be made as well, and the cord gently agitated or flow passed over the tissue to gently release cells, which are collected by centrifugation, sedimentation or filtration. If the cord is very thinly sliced or spiral sliced, the sheets can be gently agitated to release the cells, and the remaining cell free sheets can then be separated from the cells and used to make decellularized matrix.

The cell mixture is combined with the autologous serum, platelets or lysate, although syngeneic or HLA and gender matched product could be used instead. It is also possible to pool these blood products for use. The combination of mixed cells and serum, platelets or lysate can either be stored by freezing, or they can be cultured before storage, either with or without the decellularized matrix, as desired.

To make decellularized matrix, the cord portion is minced or cut into a desired shape either before or after decellularization, or both. Then the tissue is decellularized, using enzymatic, chemical, osmotic or mechanical means, but preferably avoiding harsh chemicals or enzymes that might be difficult to eliminate or might change the matrix in any way. A large numbers of washes ensures that the decellularized matrix is free of any reagents, and the matrix can be frozen, or freeze dried, or used right away. Further, it can be frozen with cord cell mixtures and/or serum, etc., or not, as desired. The resulting decellularized tissue product can be further cut into desired shape that allows the flexibility for future 3D culturing and/or differentiation of stem cells under various circumstances for tissue engineering or regenerative therapies.

FIG. 4A is a side view of how to mechanically slice cord tissue before or after decellularization. FIG. 4B is a cross-section of the umbilical cord, illustrating an example of the cutting/paring path around the vessels. The umbilical cord is spirally sliced along an axis from the surface and at a desired depth with a blade or laser. As the paring progresses, the continuous paring path is illustrated in FIG. 4B, where the eventual cord matrix sheet has portions with vessel wall and portions without.

In a Class 100 or 10,000 environment, the cord is straightened or elongated by placing a long glass or metal rod in the vessels or the cord itself or both. Next, the rod is rotated over a cutting razor or laser. Adjusting the depth of the blade or laser allows us to produce matrices of different thicknesses as the cord rotates over the blade or laser, or vice versa. Consequently, sheets of cut cord are prepared and packaged in sterile packages. As an alternate method, the cord can be embedded on e.g., agar or frozen and then spiral sliced, these processes helping to support the cord as it is cut.

Figure 4E:
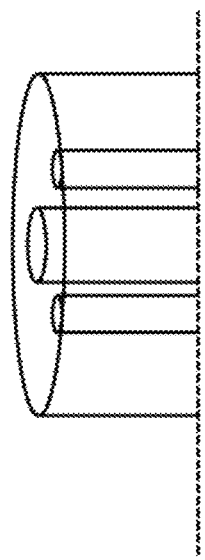
Figure 4D:
Figure 4C:
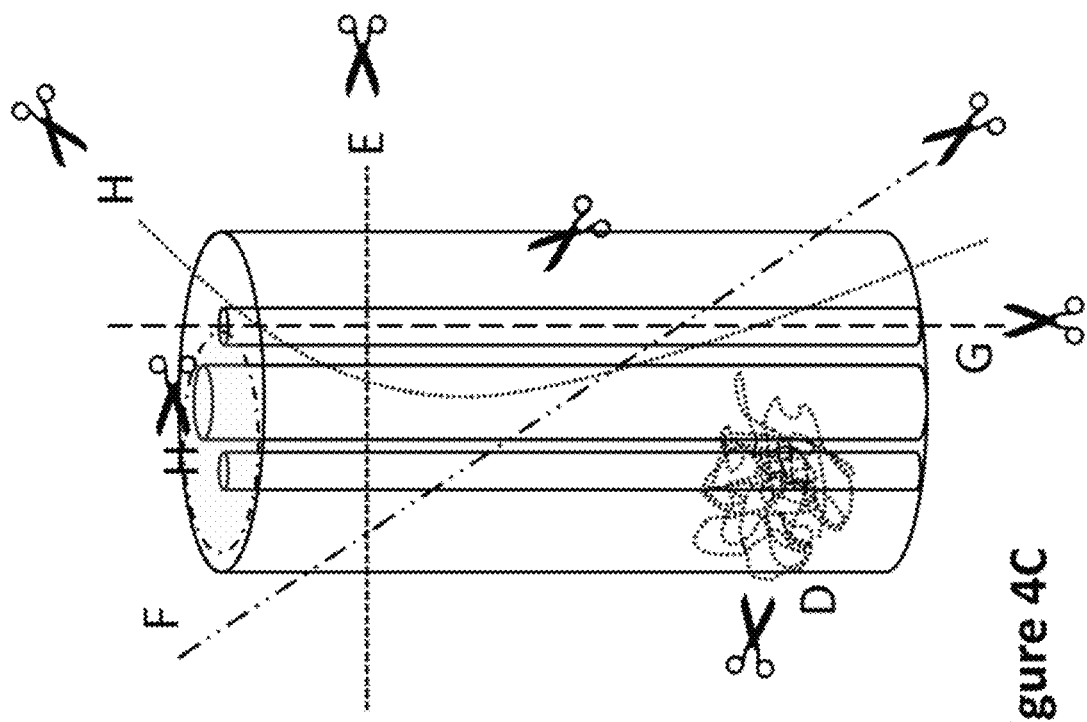
Figure 4I:
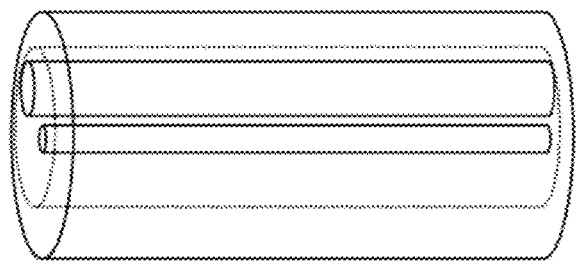
Figure 4H:
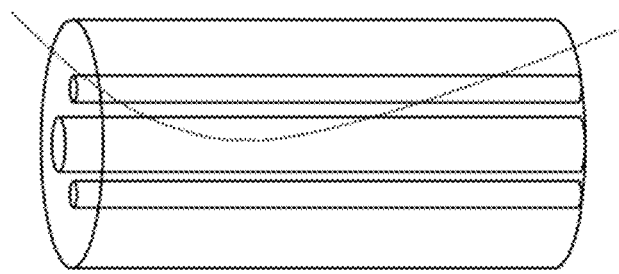
Figure 4G:
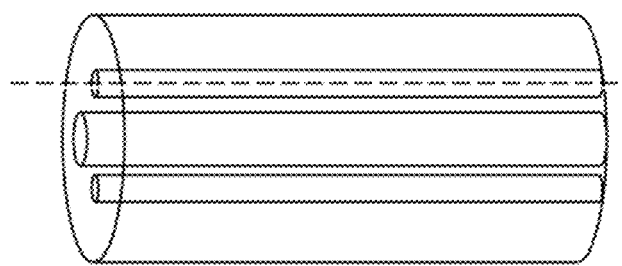
Figure 4F:
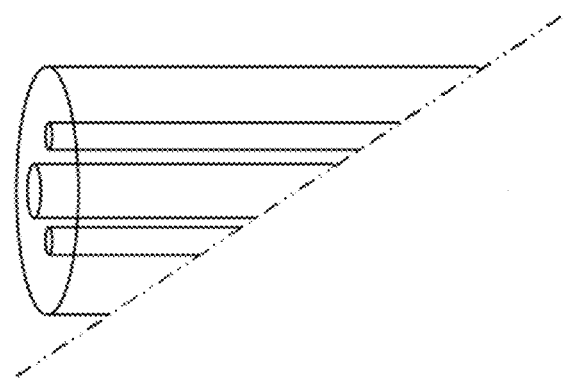
Figure 5:
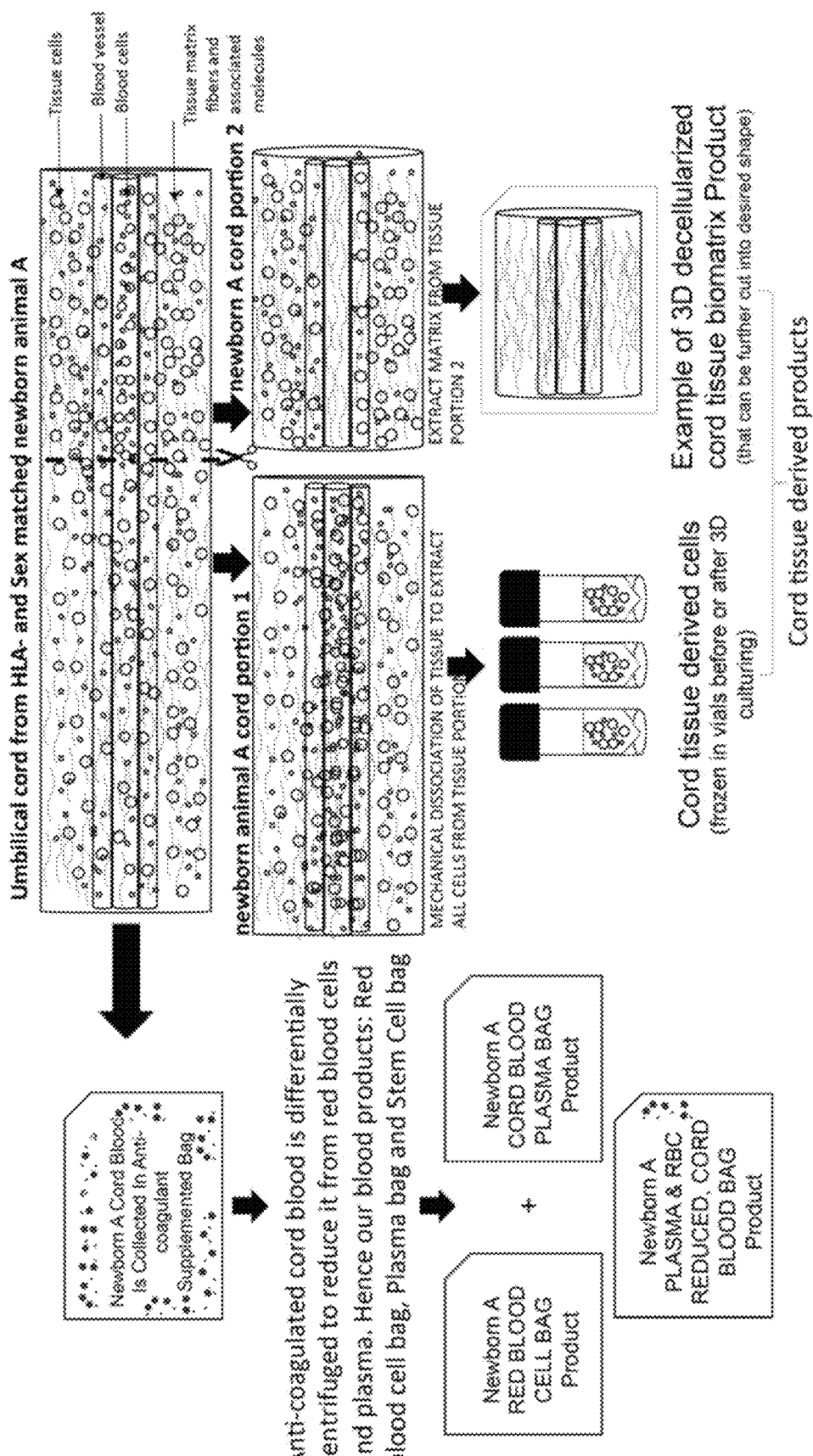
FIG. 5 is another illustration of products derived from each umbilical cord.
Figure 6:
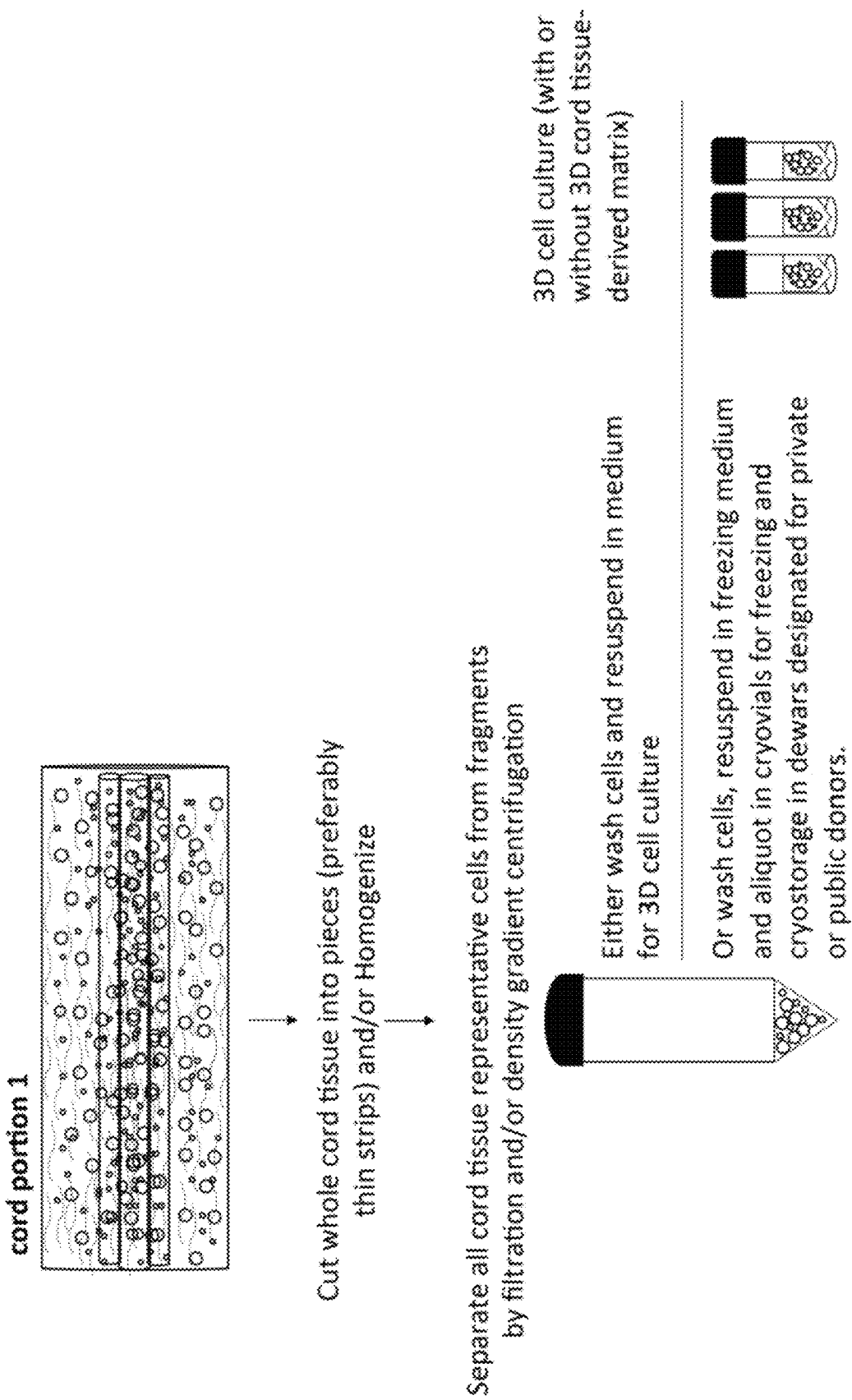
FIG. 6 Describes the process of collecting and preparing cells from a portion of the cord for freezing or 3D culturing.

Alternatively, as exemplified in FIG. 4A-I, before or after decellularization, the cord can be cut along several planes to produce different cord matrix shapes. FIG. 4A and 4B depict how a cord tissue can be sliced in sheets as the cord tissue rotates over a cutting blade or knife. The cord can also be fixed then a knife or blade cuts the cord tissue while rotating around it. FIG. 4A is a lateral view of a whole intact umbilical cord devoid of blood and without removing blood vessels it is sliced with a knife, blade or laser from the surface to produce a sheet of tissue of certain depth. FIG. 4B is a cross section or transverse view of the umbilical cord showing the cutting path that spirals from the surface inward although this spiral cutting can be made in reverse where the cord can be cored or cut from the inside towards the surface. In any case the sheet of cord retains blood vessel walls or portions of blood vessel walls. Cord tissue can also be frozen or embedded before being cut. FIG. 4C is an illustration of different cutting angles along the umbilical cord. FIG. 4D-4I show examples of different cord tissue cutting angles or paths showed by dotted or dashed lines. Figure on far left shows examples of umbilical cord tissue cutting planes before or after decellularization. FIG. 4D is a random mince of tissue. FIG. 4E is a cross section. FIG. 4F is an oblique cut. FIG. 4G is a longitudinal cut. FIG. 4H is a curved cut. FIG. 4I is a cylindrical or circular cut resulting in a cord piece with or without whole vessels and with or without the original cord surface. These shapes range from a collection of small of tissue matrix particles (like a slurry) to large matrix-intact decellularized cord tissue pieces in the shape of sheet, blocks, and the like.

The cell mixture can also be cultured together with the decellularized tissue. The decellularized tissue serves as a 3D scaffold the same as what the cells experienced in vivo, thus more closely mimicking actual cell growth. Likewise, the oxygen concentration is adjusted to a range between 0.1% and 7% at 37° C., like the in vivo condition. The culture medium is supplemented with the serum, plasma or platelet lysate obtained from autologous or syngeneic cord blood or from an HLA- and sex-matched blood, therefore reducing the incompatibility issue and the risk of cross contamination.

It is to be noted that the isolated cells need not be cultured immediately after collection, because the need for such culturing may not have arisen yet. The isolated cell mixture or matrix can be preserved for private or public use until such time that a matching patient needs treatment. Further, blood samples can be collected from the donor over time to provide a sufficient source of serum/plasma/platelet lysates to supplement future cell culturing or transplantations.

It is also to be noted that the cell mixture and decellularized tissue matrices need not be cultured immediately after collection, because the need for such products may also not have arisen yet. The isolated cell mixture can be preserved for public use until such time that an HLA- and or sex matched patient needs treatment, or it can be preserved for private use by the individual that provided the cord tissue at birth. Further, HLA- and optionally sex matched blood samples can be collected from the same HLA- and optionally sex matched donors to provide a sufficient source of serum/plasma/platelet lysates to supplement future cell culturing or transplantations. Alternatively, an individual can provide his own autologous blood product for use in culturing the mixed cells and/or matrix, since when the need arises, collection of blood will typically become practical as most often the cells will not be needed until adulthood.

Methods

Intact cord is collected and sterilized by flushing cord vessels with sterile antibiotic and antimycotic containing calcium- and magnesium-free PBS. The cord surface is cleaned with regular alcohol swabs before placing in a sterile bag or container containing calcium- and magnesium-free PBS supplemented with antibiotics and antimycotics, sealed and safely placed in a 2° C. to 10° C. compartment of a temperature controlled damage resistant shipping box, shipped to the laboratory, preferably a hybrid facility and received no more than 16 hours post delivery. At the hybrid facility, private and public cord tissues are processed independently in designated areas in different ways. Cord blood is also collected and shipped to the same facility.

For cryopreserving whole cord tissue, a piece of cord tissue is cut; a sterile plastic tube is inserted in the vessels to keep them distended or straight; the tissue is placed in a sterile tube filled with low glucose Dulbecco Modified Essential Medium (DMEM) or similar medium (e.g., a variety of stem cell media are commercially available) containing antibiotics and antimycotics, such as penicillin and streptomycin respectively, with or without 5-20% final concentration of serum, plasma or platelet lysate derived from cord blood of the same or different newborn. GMP grade cryoprotectant is added to a final concentration of 1%-10% before quick or slow freezing to below −120° C. then quarantined in the gas phase of liquid nitrogen until communicable disease diagnostics is clear. At this point, the tissue is transferred to long-term gas phase liquid nitrogen dewars designated for either private or public umbilical cord donors.

To manufacture an acellular matrix that can be used in the future for autologous or allogeneic purposes to support the regeneration of bone, cartilage, skin, fat, muscle, retinal, lens and nervous tissue, a piece of cord tissue is straightened by inserting a thick glass stick in the cord vessels. Then the cord tissue is decellularized with 0.1% peracetic acid (PAA)

for 2 hours with mechanical agitation and subsequent 15 minutes wash with phosphate buffered saline (PBS) before treating the tissue with DNAse and RNAse in calcium magnesium-free PBS at 37° C. for 1 hour. Cord tissue can also be decellularized with other chemical reagents, such as hypotonic and hypertonic solutions, alcohols, SDS or other ionic or non-ionic detergents, trypsin, and the like. Mechanical dissociation methods can also be used, such as convection flow, sonication, and the like. Decellularized matrix can be derived from a portion of cord tissue that was previously cut into desired shape with a blade or laser, or triturated, or homogenized followed by decellularization with or without inserting a stick in the vessels. Therefore, acellular matrix sizes range from small particles to various sizes and shapes of cord tissue, including a natural shape, sheets, blocks, and the like.

Cord tissue matrix is then washed with calcium magnesium-free PBS and preserved by placing it low temperature resistant membranes or containers containing calcium magnesium-free PBS or medium supplemented or not with antibiotics and antimycotics, 1%-10% cryoprotection solution, plus 1-10% of autologous, syngeneic or HLA- and sex-matched serum, plasma or platelet lysate. The matrix and serum combination is then slowly and gradually or fast snap frozen to −20° C. or below.

In contrast, when the cells are to be retained, the tissue can be finely sliced, diced or homogenized without removing surface membrane or vessels and the cells gently liberated. For example, the tissue can be completely sliced into thin strips (shaved slices), or only striated partway through, and gentle rocking or convection flow applied, if needed, to free the cells from the thin piece of tissue. Cells in solution are collected and separated from tissue matrix by filtration, sedimentation or density gradient centrifugation. Cells can also be dissociated by homogenizing whole cord tissue using a mortar and pestle or a commercially available device. This method preserves the cells for subsequent use.

To isolate novel mesenchymal stem cells (along with progenitor and differentiated cells and other not yet characterized cells like non-adherent or not yet surface adhering cells), cord tissue is mechanically dissociated or cut within 16 hours of delivery into thin filaments (including vessel walls) using a sterile scalpel or homogenizer and then liberated single and clumped cells still attached to some cord tissue matrix are directly frozen slowly or quickly to below −120° C. in medium containing 1%-10% cryoprotectant preferably supplemented with serum, plasma or platelet lysate derived from the same newborn. Alternatively, isolated single cells and clumps of cells still attached to some cord tissue matrix are placed in suspension to be cultured for days or months in a prior art 3D chamber, preferably in 0.5%-7% oxygen pressure, humidified $CO_2$ and $N_2$ gas environment and a low glucose DMEM medium, preferably supplemented with either serum, plasma or platelet lysate derived from the same newborn. The cells can also be cultured for days or months on a cord tissue-derived biomatrix having a certain desired 3D shape. Blood components can also be isolated from the same person or animal later in life, thus maintaining a source of autologous blood components as long as possible.

Although there exists a controversy over the expression of "mesenchymal stem cells" markers, the isolated cord tissue-derived cells contains a pool of cells with the following surface markers when grown in 2-dimensional culture in the presence of fetal bovine serum: $CD10^{30}$, $CD29^{+++}$, $CD44^{+++}$, $CD73^{++}$, $CD54^+$, $CD58^+$, $CD105^+$, low $CD106^+$, $CD146^+$, $CD166^+$, low HLA-ABC$^+$, STRO-1$^+$. Gatta V. et. al., (2013) Gene expression modifications in Wharton's Jelly mesenchymal stem cells promoted by prolonged in vitro culturing. BMC Genomics 2013, 14:635; Arutyunyan I. et. al., (2016) Umbilical Cord as Prospective Source for Mesenchymal Stem Cell-Based Therapy. Stem Cells International Article ID 6901286.

The different plus signs define the degree of a marker's expression whereby one plus sign means little expression and more plus signs mean higher expression. Another isolated pool of cord tissue-derived cells do not have the following surface markers when grown in 2-dimensional culture in the presence of fetal bovine serum: $CD3^-$, $CD7^-$, $CD19^-$, $CD14^-$, $CD28^-$, $CD31^-$, $CD33^-$, $CD34^-$, $CD38^-$, $CD40^-$, $CD45^-$, $CD56^-$, $CD62L^-$, $CD62P^-$, $CD80^-$, $CD86^-$, $CD90^-$, $CD106^-$, $CD117^-$, $CD133^-$, $CD135^-$, $CD144^-$, $CD271^-$, $CD326^-$, HLA-DR$^-$, Lin C. S., Ning H., Lin G., Lue T. F. (2012) Is CD34 truly a negative marker for mesenchymal stromal cells? Cytotherapy 14:1159-1163. Imran Ullah I. et. al., (2015) Human mesenchymal stem cells—current trends and future prospective. Bioscience Reports 35/art:e00191. Still another pool of isolated cord tissue-derived cells has the following markers: CD31, CD34, CD105, CD146, VE-Cadherin, VEGFR1, VEGFR2, Tie2, CXCR4, Von Willebrand, Aldehyde dehydrogenase but does not express CD1, CD115, CD45 and CD133. However, with our cell culture methods we expect these cells to have a different molecular marker signature and/or strength of marker expression. These surface markers can be used to further characterize and/or isolate cells of various differentiation potentials when cultured in 3D and/or in the presence of 0.5%-7% (or preferably 0.5%-5%) oxygen and/or in the presence of serum, plasma or platelet lysate derived from an HLA- and optionally sex-matched animal.

Figure 7:
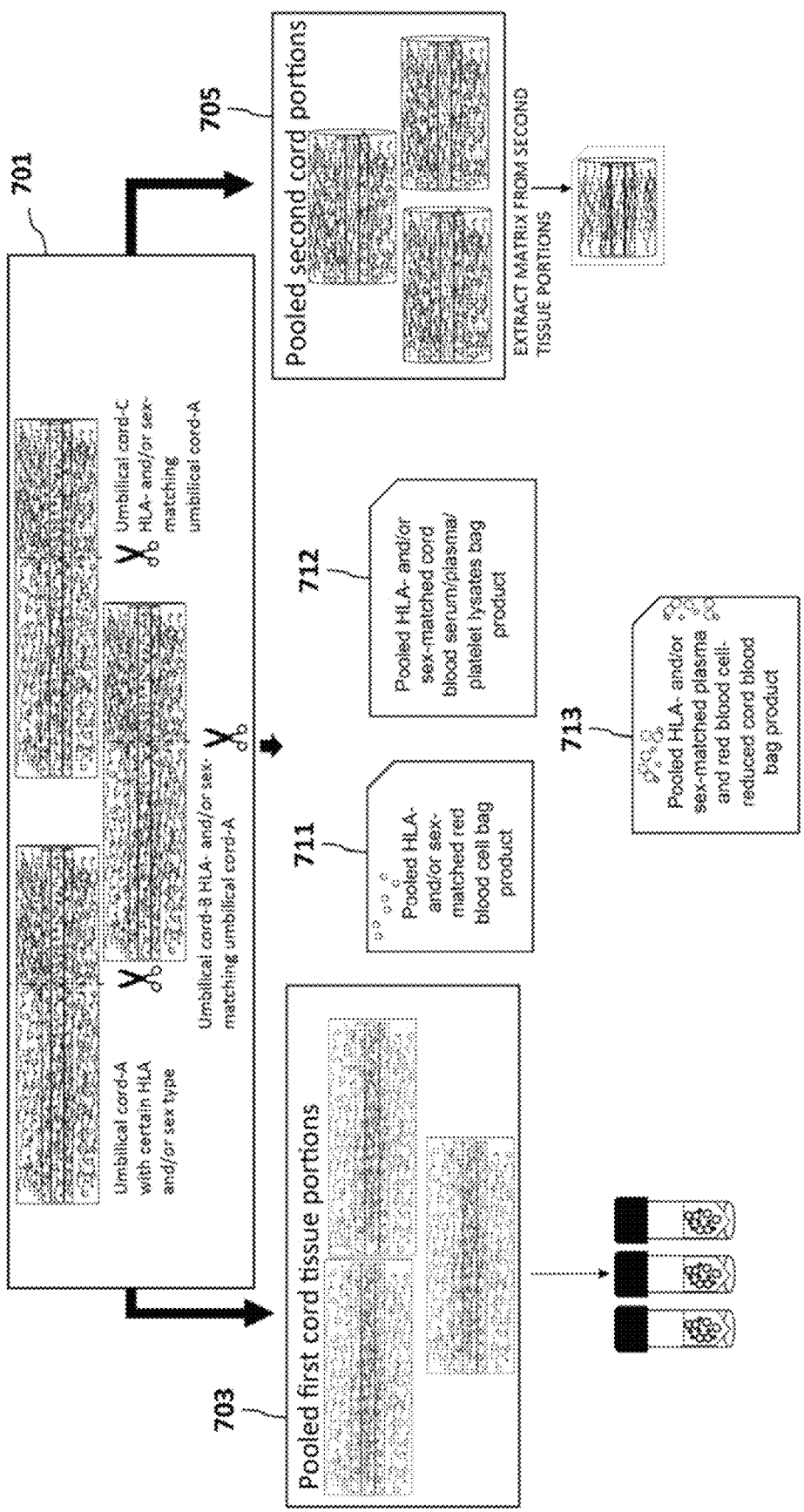
FIG. 7 Describes the process of pooling cord cells and cord tissues from more than one donors.

The cord blood, tissue cells and tissues biomatrix may be pooled from more than one donors, as long as the donors are HLA- and optionally sex-matched. The process is shown in FIG. 7 that shows an example of umbilical cord blood, cord tissue cells and cord tissue matrix products pooled from three HLA- and optionally sex-matching umbilical cords. In Step 701, three umbilical cord from three HLA-matching and optionally sex-matching donor animals are obtained. Each cord is then cut into two portions, and the cord blood from each cord is processed. Anticoagulated blood is first collected from each cord then processed into serum or plasma and blood stem cell bag products. From each cord blood processed, collect: one red blood cell (RBC) bag product; one plasma bag product; one plasma- & RBC-reduced cord blood bag product, and then pool each HLA- and optionally sex-matched product type into one bag.

In Step 703, portions for deriving cells are pooled together, by mechanical dissociation of tissue to extract all cells from the first cord portion. Example of pooled HLA- and/or sex-matched cord tissue-derived cells product is shown, and optionally being frozen in sterile vials.

In step 705, portions for deriving matrices are pooled together, by extracting biomatrix from the second cord portion. Example of Pooled HLA- and/or sex matched 3D decellularized cord tissue biomatrix product that can be further cut into desired shape, and optionally frozen in sterile container.

In some instances where a patient has not saved his or her umbilical cord, or when a newborn is affected by a genetic disease, it is best to treat that individual with cell and matrix products derived from HLA matching and preferably sex matching donors. The greater the HLA and sex match the greater the chance of engraftment and tolerance of transplanted cells, matrices and tissues.

Before or after culture, HLA- and optionally sex-matched cells and matrices cultured alone or in combination are collected and a sample is characterized by some or all of the following: sterility, size, cell surface and intracellular markers, cell proliferation rate, cell self-renewal and differentiation potential, matrix strength and cell infiltration, using microscopy, flow cytometry, cell and molecular biology techniques, as well as engraftment and regeneration assays in animal models. Concurrently, all cells are collected, washed and suspended in fresh medium containing HLA and/or sex matched cord blood serum, plasma or platelet lysate and 1% to 10% GMP grade cryoprotectant before slow and gradual or fast freezing to −120° C. or below, then quarantined in the gas phase of liquid nitrogen until communicable disease diagnostics is clear. Until then, the cells or tissues are transferred to long-term gas phase liquid nitrogen dewars designated for either private or public umbilical cord donors.

Figure 2:
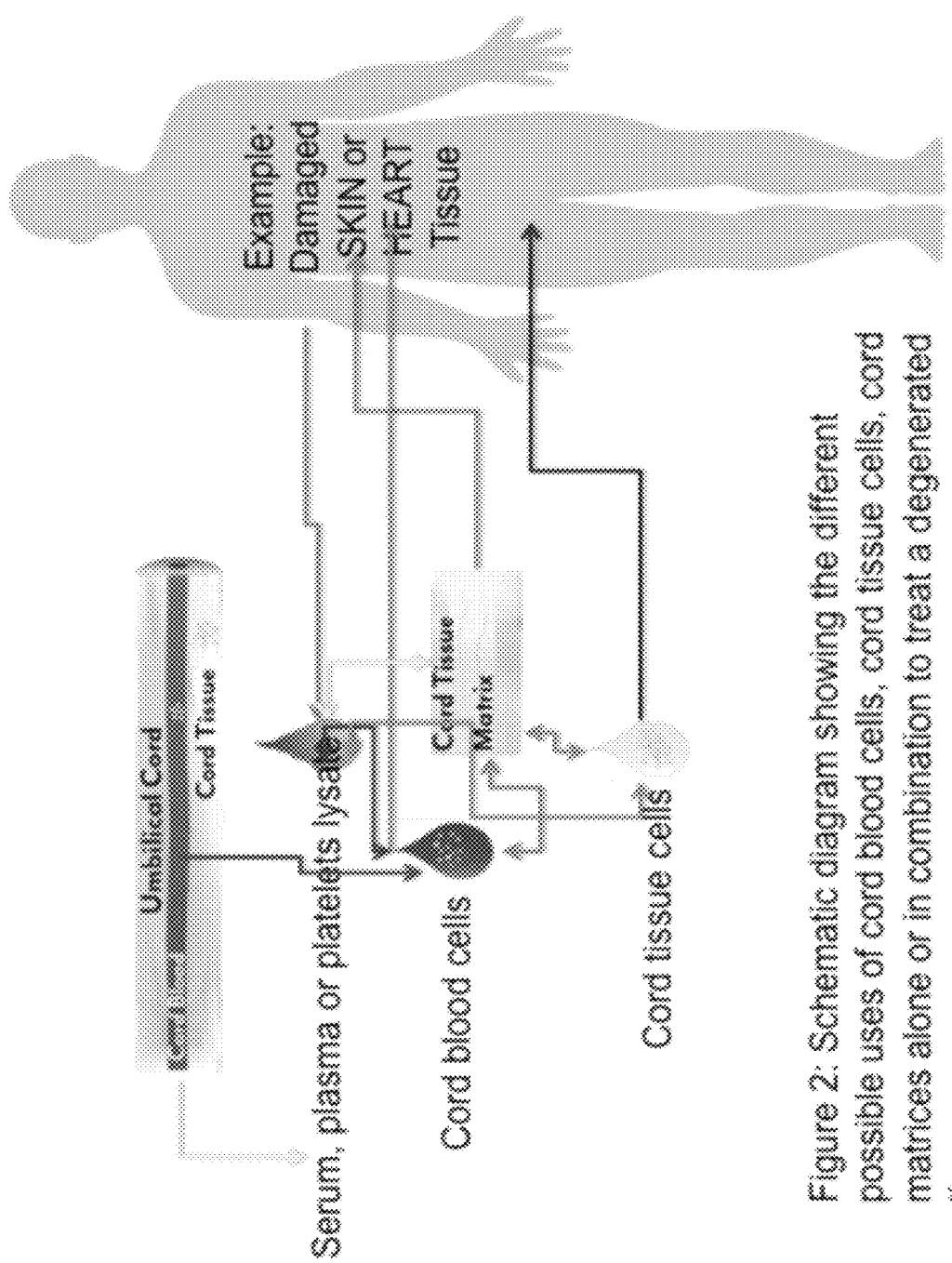
FIG. 2 is a schematic diagram illustrating possible combination of cord blood cells, cord blood serum/plasma or platelets lysate, cord tissue cells and cord matrices products, singly or combination thereof to treat a degenerated tissue.
Figure 3:
FIG. 3 is a schematic diagram illustrating the development process of cells.

On use, the cells can be allowed to attach or are reinfused back in the decellularized tissue biomatrix of a desired shape. This is done by combining the two using varying concentration of cells and decellularized tissue biomatrices and allowing the cells to attach and diffuse into the matrix, or by injecting them thereinto, depending on matrix shape and size. The cells can be used alone, but the decellularized tissue matrix provides a useful 3D scaffold and a regulated environment for stem cell maintenance and growth, and is a preferred methodology. Umbilical cord derived cells and decellularized tissue matrix can be used alone or in any combinations for animal or human therapeutic purposes. See FIG. 1, FIG. 2, Table 1, Table 2, Table 3, Table 4, and Table 5.

Although various embodiments of the method and apparatus of the present disclosure have been illustrated in the accompanying Drawings (FIGS. 1 through 7 and Tables 1 through 5) and described in the foregoing Detailed Description, it will be understood that the disclosure is not limited to the embodiments disclosed, but is capable of numerous rearrangements, modifications and substitutions without departing from the spirit of the disclosure as set forth herein.

The following are each incorporated by reference herein in its entirety for all purposes:

Gerlach J C, et al., Dynamic 3D culture promotes spontaneous embryonic stem cell differentiation in vitro, Tissue Eng Part C Methods. 2010 Feb;16(1):115-21.

Bosch J, et al., Distinct Differentiation Potential of "MSC" Derived from Cord Blood and Umbilical Cord: Are Cord-Derived Cells True Mesenchymal Stromal Cells?, Stem Cells and Development (2012).

U.S. application Ser. No. 13/890,134, filed May 8, 2013, and 61/644,423, filed May 8, 2012.

U.S. Pat. No. 8,656,670 Facilities for hybrid tissue banks

Akkermann R., Beyer F., Küry P. (2017) "Heterogeneous populations of neural stem cells contribute to myelin repair", Neural Regen Res. Apr;12(4):509-517.

Arutyunyan I. et. al., (2016) Umbilical Cord as Prospective Source for Mesenchymal Stem Cell-Based Therapy. Stem Cells International Article ID 6901286.

Badylak Steven (2014) Decellularized Allogeneic and Xenogeneic Tissue as a Bioscaffold for Regenerative Medicine: Factors that Influence the Host Response. Annals of Biomedical Engineering, Vol. 42, No. 7.

DeLima M. et. al., (2012) Cord-Blood Engraftment with Ex Vivo Mesenchymal-Cell Coculture, NEJM 367;24.

De Waele M. et. al., (2004) Growth factor receptor profile of CD34+ cells in normal bone marrow, cord blood and mobilized peripheral blood. Eur J Haematol. Mar;72(3):193-202.

Emnett R. J. et. al., (2016) Evaluation of Tissue Homogenization to Support the Generation of GMP-Compliant Mesenchymal Stromal Cells from the Umbilical Cord. Stem Cells International. Article ID 3274054.

Friedman R. et. al., (2007) Umbilical Cord Mesenchymal Stem Cells: Adjuvants for Human Cell Transplantation. Biology of Blood and Marrow Transplantation 13:1477-1486.

Gatta V. et. al., (2013) Gene expression modifications in Wharton's Jelly mesenchymal stem cells promoted by prolonged in vitro culturing. BMC Genomics 2013, 14:635.

Gentile P. et. al., (2017) Concise Review: The Use of Adipose-Derived Stromal Vascular Fraction Cells and Platelet Rich Plasma in Regenerative Plastic Surgery. Stem Cells;35:117-134.

Gharibi B., Hughes F. J., (2012) Effects of Medium Supplements on Proliferation, Differentiation Potential, and In Vitro Expansion of Mesenchymal Stem Cells, Stem Cells Translational Medicine, 1:771-782.

Imran Ullah I. et. al., (2015) Human mesenchymal stem cells—current trends and future prospective. Bioscience Reports 35/art:e00191.

Jung J, Moon N, Ahn J Y, et al. Mesenchymal stromal cells expanded in human allogenic cord blood serum display higher self-renewal and enhanced osteogenic potential. Stem Cells and Development. 2009;18(4):559-571.

Keating, A. (2012) "Mesenchymal Stromal Cells: New Directions", Cell Stem Cell 10, 709-716.

Lin C. S., Ning H., Lin G., Lue T. F. (2012) Is CD34 truly a negative marker for mesenchymal stromal cells? Cytotherapy 14:1159-1163.

Lo Sardo, V. et al. (2017) Influence of donor age on induced pluripotent stem cells. Nat. Biotechnol. 35,69-74.

McNiece I, Gluckman E, Wagner J E, et al. Ex vivo expansion of umbilical cord blood hemopoietic stem and progenitor cells. Exp Hematol. 2004;32:409-413.

Mendicino M., Bailey A. M., Wonnacott K., Puri R. K., Bauer S. R., (2014) "MSC-Based Product Characterization for Clinical Trials: An FDA Perspective", Cell Stem Cell 14, Feb 6.

Meral Beksac (2016) How to Improve Cord Blood Transplantation. By Enhancing Cell Count or Engraftment? Frontiers in Medicine, Vol. 3, Article 20.

Phadnis S M, Joglekar M V, Venkateshan V, Ghaskadbi S M, Hardikar A A, Bhonde R R. Human umbilical cord blood serum promotes growth, proliferation, as well as differentiation of human bone marrow-derived progenitor cells. In Vitro Cellular and Developmental Biology-Animal. 2006;42(10):283-286

Shakouri-Motlagh A. et. al., (2017) Native and solubilized decellularized extracellular matrix: A critical assessment of their potential for improving the expansion of mesenchymal stem cells. Acta Biomaterialia 55 (2017) 1-12.

Sharpless N. E. and De Pinho R. A., (2007) "How stem cells age and why this makes us grow old", Nature Rev. Mol. Cell Biol.

Shu S. et. al., (2012), "Immunogenicity of allogeneic mesenchymal stem cells" J. Cell. Mol. Med. Vol 16, No 9, pp. 2094-2103.

Shuvalova N. S. et. al., (2013), "Maintenance of mesenchymal stem cells culture due to the cells with reduced attachment rate" Biopolymers and Cell. Vol. 29. N 1. P. 75-78

Sisakhtnezhad S., Alimoradi E., Akrami H., (2017) External factors influencing mesenchymal stem cell fate in vitro, European Journal of Cell Biology, Vol 96, Issue 1, Pages 13-33.

Wagner J E. et. al., (2002) "Transplantation of unrelated donor umbilical cord blood in 102 patients with malignant and nonmalignant diseases: influence of CD34 cell dose and HLA disparity on treatment-related mortality and survival". Blood, 100:1611-1618.

TABLE 1

| Each row refers to the product(s) marked by "X" delivered before or after 3D culture for research or transplantation in an HLA-and/or sex matched patient | AUTOLOGOUS PRODUCTS FROM ONE DONOR | | | | |
|---|---|---|---|---|---|
| | Serum, Plasma or Platelet Lysate from newborn A | Umbilical Cord Blood Cells from newborn A | Umbilical Cord Tissue Cells from newborn A | Whole Umbilical Cord Tissue Matrix from newborn A | |
| 1 | X | | | | DELIVERED BEFORE OR AFTER 3D CULTURE IN OR WITHOUT HYPOXIA FOR RESEARCH OR TRANSPLANTATION IN AN HLA- AND/OR SEX MATCHED PATIENT |
| 2 | X | X | | | |
| 3 | X | X | X | | |
| 4 | X | X | X | X | |
| 5 | X | X | | X | |
| 6 | X | | X | | |
| 7 | X | | | X | |
| 8 | X | | X | X | |
| 9 | | X | | | |
| 10 | | X | X | | |
| 11 | | X | | X | |
| 12 | | X | X | X | |
| 13 | | | X | | |
| 14 | | | | X | |
| 15 | | | X | X | |

TABLE 2

| Each row refers to the product(s) marked by "X" delivered before or after 3D culture for research or transplantation in an HLA-and/or sex matched patient | AUTOLOGOUS PRODUCTS FROM ONE DONOR | | | Allogeneic Product Pooled HLA- and/or Sex Matching Whole Umbilical Cord Tissue Matrix (taken from donors) | |
|---|---|---|---|---|---|
| | Serum, Plasma or Platelet Lysate from newborn A | Umbilical Cord Blood Cells from newborn A | Umbilical Cord Tissue Cells from newborn A | | |
| 1 | X | | | | DELIVERED BEFORE OR AFTER 3D CULTURE IN OR WITHOUT HYPOXIA FOR RESEARCH OR TRANSPLANTATION IN AN HLA- AND/OR SEX MATCHED PATIENT |
| 2 | X | X | | | |
| 3 | X | X | X | | |
| 4 | X | X | X | X | |
| 5 | X | X | | X | |
| 6 | X | | X | | |
| 7 | X | | | X | |
| 8 | X | | X | X | |
| 9 | | X | | | |
| 10 | | X | X | | |
| 11 | | X | | X | |
| 12 | | X | X | X | |
| 13 | | | X | | |
| 14 | | | | X | |
| 15 | | | X | X | |

TABLE 3

| Each row refers to the product(s) marked by "X" delivered before or after 3D culture for research or transplantation in an HLA-and/or sex matched patient | Allogeneic Product Pooled HLA-and/or Sex matching sera/plasmas or platelet lysates (taken from donors) | AUTOLOGOUS PRODUCTS FROM ONE DONOR | | | |
|---|---|---|---|---|---|
| | | Umbilical Cord Blood Cells from newborn A | Umbilical Cord Tissue Cells from newborn A | Whole Umbilical Cord Tissue Matrix from newborn A | |
| 1 | X | | | | DELIVERED BEFORE OR AFTER 3D CULTURE IN OR WITHOUT HYPOXIA FOR RESEARCH OR TRANSPLANTATION IN |
| 2 | X | X | | | |
| 3 | X | X | X | | |
| 4 | X | X | X | x | |
| 5 | X | X | | x | |

TABLE 3-continued

| Each row refers to the product(s) marked by "X" delivered before or after 3D culture for research or transplantation in an HLA-and/or sex matched patient | Allogeneic Product Pooled HLA-and/or Sex matching sera/plasmas or platelet lysates (taken from donors) | AUTOLOGOUS PRODUCTS FROM ONE DONOR | | | Whole Umbilical |
|---|---|---|---|---|---|
| | | Umbilical Cord Blood Cells from newborn A | Umbilical Cord Tissue Cells from newborn A | Cord Tissue Matrix from newborn A | |
| 6 | X | | X | | AN HLA- AND/OR SEX MATCHED PATIENT |
| 7 | X | | | X | |
| 8 | X | | X | X | |
| 9 | | X | | | |
| 10 | | X | X | | |
| 11 | | X | | X | |
| 12 | | X | X | X | |
| 13 | | | X | | |
| 14 | | | | X | |
| 15 | | | X | X | |

TABLE 4

| Each row refers to the product(s) marked by "X" delivered before or after 3D culture for research or transplantation in an HLA-and/or sex matched patient | Allogeneic Product Pooled HLA- and/or Sex matching sera/plasmas or platelet lysates (taken from donors) | Autologous Products from Same Donor | | Allogeneic Product Pooled HLA- and/or Sex Matching Whole Umbilical Cord Tissue Matrix (taken from same pool of sera donors) | |
|---|---|---|---|---|---|
| | | Umbilical Cord Blood Cells from newborn A | Umbilical Cord Tissue Cells from newborn A | | |
| 1 | X | | | | DELIVERED BEFORE OR AFTER 3D CULTURE IN OR WITHOUT HYPOXIA FOR RESEARCH OR TRANSPLANTATION IN AN HLA- AND/OR SEX MATCHED PATIENT |
| 2 | X | X | | | |
| 3 | X | X | X | | |
| 4 | X | X | X | X | |
| 5 | X | X | | X | |
| 6 | X | | X | | |
| 7 | X | | | X | |
| 8 | X | | X | X | |
| 9 | | X | | | |
| 10 | | X | X | | |
| 11 | | X | | X | |
| 12 | | X | X | X | |
| 13 | | | X | | |
| 14 | | | | X | |
| 15 | | | X | X | |

TABLE 5

| Each row refers to the product(s) marked by "X" delivered before or after 3D culture for research or transplantation in an HLA-and/or sex matched patient | Pooled HLA- and/or Sex matching sera/plasmas or platelet lysates (taken from donors) | Pooled Umbilical Cord Blood Cells from HLA- and/or Sex matched patient (taken from same pool of sera donors) | Umbilical Cord Tissue Cells HLA- and/or Sex matched patient (taken from same pool of sera and cord blood donors) | Pooled HLA- and/or Sex Matching Whole Umbilical Cord Tissue Matrix (taken from same pool of sera and cord blood and cord tissue cells donors) | |
|---|---|---|---|---|---|
| 1 | X | | | | DELIVERED BEFORE OR AFTER 3D CULTURE IN OR WITHOUT HYPOXIA FOR RESEARCH OR TRANSPLANTATION IN AN HLA- AND/OR SEX MATCHED PATIENT |
| 2 | X | X | | | |
| 3 | X | X | X | | |
| 4 | X | X | X | X | |
| 5 | X | X | | X | |
| 6 | X | | X | | |
| 7 | X | | | X | |
| 8 | X | | X | X | |
| 9 | | X | | | |
| 10 | | X | X | | |
| 11 | | X | | X | |

TABLE 5-continued

| Each row refers to the product(s) marked by "X" delivered before or after 3D culture for research or transplantation in an HLA-and/or sex matched patient | Pooled HLA- and/or Sex matching sera/ plasmas or platelet lysates (taken from donors) | Pooled Umbilical Cord Blood Cells from HLA- and/or Sex matched patient (taken from same pool of sera donors) | Umbilical Cord Tissue Cells HLA- and/or Sex matched patient (taken from same pool of sera and cord blood donors) | Pooled HLA- and/or Sex Matching Whole Umbilical Cord Tissue Matrix (taken from same pool of sera and cord blood and cord tissue cells donors) |
|---|---|---|---|---|
| 12 | | X | X | X |
| 13 | | X | X | |
| 14 | | | | X |
| 15 | | | X | X |

I claim:

1. A method of culturing stem cells, said method comprising:
   a) obtaining a mixture of cells from umbilical cord tissue, said mixture of cells including differentiated cells, stem cells and progenitor cells;
   b) obtaining plasma, serum or platelet lysate that is HLA-matched and optionally gender matched to said mixture of cells and having at least 3 MEW loci that are matched to said mixture of cells; and
   c) culturing said mixture of cells under hypoxic (0.1-7% O$_2$) conditions in a medium supplemented with 1-10% of said plasma, serum or platelet lysate.

2. The method of claim 1, wherein said culturing in step c) is three dimensional (3D) culturing in a decellularized tissue biomatrix.

3. The method of claim 2, wherein said biomatrix is from umbilical cord.

4. The method of claim 1, wherein said serum, plasma or platelet lysate is a pooled HLA-matched product, each pooled portion of said pooled HLA-matched product having a same at least 3 matched MEW loci.

5. The method of claim 2, wherein said biomatrix is obtained by steps consisting essentially of:
   i) obtaining an intact portion of umbilical cord tissue;
   ii) cleaning said intact portion of umbilical cord tissue with a sterilizing agent;
   iii) decellularizing said intact portion of umbilical cord tissue to produce a decellularized tissue;
   iv) cutting said decellularized tissue to a desired shape without removing surface membranes or blood vessels; and
   v) incubating said decellularized tissue with serum, plasma or platelet lysate in 0.1% to 5% oxygen environment to make said biomatrix; and
   vi) combining said biomatrix and said mixture of cells for said culturing step c.

6. The method of claim 2, wherein said mixture of cells and said biomatrix are obtained by a method comprising:
   i) obtaining a first umbilical cord tissue from a first newborn animal;
   ii) cleaning said first umbilical cord tissue with a sterilizing agent;
   iii) mechanically dissociating said first umbilical cord tissue to isolate said mixture of cells from said first umbilical cord tissue without separating vessels from said first umbilical cord tissue;
   iv) obtaining a second umbilical cord tissue from said first newborn animal or from a second newborn animal;
   v) cutting said second umbilical cord tissue to a desired shape without separating vessels from said second umbilical cord tissue and decellularizing said second umbilical cord tissue to produce said decellularized tissue biomatrix;
   vi) culturing said mixture of cells together with said biomatrix in step c) wherein said serum, plasma or platelet lysate is from said first newborn animal.

7. The method of claim 6, wherein said mixture of cells and said serum, plasma or platelet lysate are each a pooled HLA-matched product, each pooled portion of said pooled HLA-matched product having a same at least 3 matched MHC loci.

8. A method of culturing stem cells, said method comprising:
   a) obtaining stem cells;
   b) obtaining plasma, serum or platelet lysate that is HLA-matched and optionally gender matched to said stem cells and having at least 3 MHC loci that are matched to said stem cells;
   c) culturing said stem cells under hypoxic (0.1-7% O$_2$) conditions in a three dimensional (3D) biomatrix comprising decellularized cord tissue plus a medium supplemented with 1-10% of said plasma, serum or platelet lysate.

9. The method of claim 8, wherein said stem cells and said serum, plasma or platelet lysate are each a pooled HLA-matched product, each pooled portion of said pooled HLA-matched product having a same at least 3 matched MHC loci.

10. The method of claim 8, wherein said biomatrix is obtained by steps consisting essentially of:
    i) obtaining an intact portion of umbilical cord tissue;
    ii) cleaning said intact portion of umbilical cord tissue with a sterilizing agent;
    iii) decellularizing said intact portion of umbilical cord tissue to produce a decellularized tissue;
    iv) cutting said decellularized tissue to a desired shape without removing surface membranes or blood vessels;
    v) incubating said decellularized tissue with serum, plasma or platelet lysate in 0.1% to 5% oxygen environment to produce said biomatrix; and
    vi) combining said biomatrix with said stem cells for said culturing step c.

11. The method of claim 8, wherein said stem cells and said biomatrix are obtained by a method comprising:
    i) obtaining a first umbilical cord tissue from a first newborn animal;
    ii) cleaning said first umbilical cord tissue with a sterilizing agent;
    iii) mechanically dissociating said first umbilical cord tissue to isolate said stem cells from said first umbilical cord tissue without separating vessels from said first umbilical cord tissue, wherein said stem cells are a mixture of differentiated cells, stem cells and progenitor cells;

iv) obtaining a second umbilical cord tissue from said first newborn animal or from a second newborn animal;

v) cutting said second umbilical cord tissue to a desired shape without separating vessels from said second umbilical cord tissue and decellularizing said second umbilical cord tissue to produce said decellularized tissue biomatrix;

vi) culturing said stem cells together with said biomatrix in step c) wherein said serum, plasma or platelet lysate is from said first newborn animal.

12. The method of claim 11, wherein said stem cells and said serum, plasma or platelet lysate are each a pooled HLA-matched product, each pooled portion of said pooled HLA-matched product having a same at least 3 matched MHC loci.

\* \* \* \* \*

UNITED STATES PATENT AND TRADEMARK OFFICE
CERTIFICATE OF CORRECTION

PATENT NO. : 11,760,976 B2  
APPLICATION NO. : 17/081701  
DATED : September 19, 2023  
INVENTOR(S) : Raymond Mouzannar Page 1 of 1

It is certified that error appears in the above-identified patent and that said Letters Patent is hereby corrected as shown below:

In the Claims

On Column 31, Line 24, of Claim 1:
"mixture of cells and having at least 3 MEW loci that are"
Should read as:
---mixture of cells and having at least 3 MHC loci that are---

On Column 31, Line 38, of Claim 4:
"a same at least 3 matched MEW loci."
Should read as:
---a same at least 3 matched MHC loci.---

Signed and Sealed this
Twenty-fourth Day of October, 2023

Katherine Kelly Vidal
*Director of the United States Patent and Trademark Office*